United States Patent
Grygus et al.

(10) Patent No.: US 11,478,588 B2
(45) Date of Patent: Oct. 25, 2022

(54) NEEDLE SHIELD GRIP DEVICES AND RELATED METHODS

(71) Applicant: Regeneron Pharmaceuticals, Inc., Tarrytown, NY (US)

(72) Inventors: Bryan Grygus, Clifton Park, NY (US); Richard Jeff Gildersleeve, Maple Grove, MN (US); Shaina Varghese, Green Island, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 311 days.

(21) Appl. No.: 16/574,327

(22) Filed: Sep. 18, 2019

(65) Prior Publication Data
US 2020/0093995 A1   Mar. 26, 2020

Related U.S. Application Data

(60) Provisional application No. 62/734,665, filed on Sep. 21, 2018.

(51) Int. Cl.
*A61M 5/32* (2006.01)
*B29C 45/14* (2006.01)
(Continued)

(52) U.S. Cl.
CPC ..... *A61M 5/3204* (2013.01); *B29C 45/14819* (2013.01); *B29C 45/2602* (2013.01);
(Continued)

(58) Field of Classification Search
CPC .............. A61M 5/3204; A61M 5/3202; A61M 2205/586; A61M 2205/58; A61M 5/3216;
(Continued)

(56) References Cited

U.S. PATENT DOCUMENTS

D641,078 S   7/2011 Morgan et al.
D653,336 S   1/2012 Morgan et al.
(Continued)

FOREIGN PATENT DOCUMENTS

DE   20 2009 019 162 U1   7/2017
EP        2923716 A1   9/2015
(Continued)

OTHER PUBLICATIONS

"Opening", 2022, https://www.dictionary.com/browse/opening (Year: 2022).*

(Continued)

*Primary Examiner* — Theodore J Stigell
*Assistant Examiner* — Rachel T. Smith
(74) *Attorney, Agent, or Firm* — Bookoff McAndrews, PLLC

(57) ABSTRACT

A needle guard grip device may include a body extending from a first end to a second end along a central longitudinal axis of the body. The body may include a plurality of ribs extending perpendicularly to the central longitudinal axis. The plurality of ribs may include a first set of longitudinally spaced ribs disposed on a first side of the central longitudinal axis, and a second set of longitudinally spaced ribs disposed on a second side of the central longitudinal axis that is opposite of the first side. Moving along the central longitudinal axis, ribs of the first set of longitudinally spaced ribs may alternate with ribs of the second set of longitudinally spaced ribs.

20 Claims, 17 Drawing Sheets

(51) Int. Cl.
*B29C 45/26* (2006.01)
*F16B 2/24* (2006.01)
*B29L 31/00* (2006.01)

(52) U.S. Cl.
CPC ......... *F16B 2/245* (2013.01); *A61M 2207/00* (2013.01); *B29L 2031/7544* (2013.01)

(58) Field of Classification Search
CPC .............. A61M 5/326; A61M 25/0618; A61M 5/3243; A61M 25/0631; A61B 5/150259; A61B 2017/00424
See application file for complete search history.

(56) References Cited

U.S. PATENT DOCUMENTS

| | | |
|---|---|---|
| D660,419 S | 5/2012 | Morgan et al. |
| D660,958 S | 6/2012 | McLoughlin et al. |
| D661,389 S | 6/2012 | Morgan et al. |
| D676,552 S | 2/2013 | McLoughlin et al. |
| 8,529,518 B2 | 9/2013 | Larsen et al. |
| 8,579,866 B2 | 11/2013 | Morgan et al. |
| 8,708,968 B2 | 4/2014 | Julian et al. |
| 8,945,065 B2 | 2/2015 | Torris et al. |
| 8,945,067 B2 | 2/2015 | McLoughlin et al. |
| 9,339,610 B2 | 5/2016 | Julian et al. |
| 9,757,513 B2 | 2/2017 | McLoughlin et al. |
| 9,669,158 B2 | 6/2017 | McLoughlin et al. |
| 9,757,521 B2 | 9/2017 | McLoughlin et al. |
| 9,757,524 B2 | 9/2017 | McLoughlin et al. |
| 9,764,084 B2 | 9/2017 | McLoughlin et al. |
| 9,764,101 B2 | 9/2017 | McLoughlin et al. |
| 9,789,254 B2 | 10/2017 | McLoughlin et al. |
| 9,795,734 B2 | 10/2017 | McLoughlin et al. |
| 9,808,575 B2 | 11/2017 | McLoughlin et al. |
| 9,821,123 B2 | 11/2017 | McLoughlin et al. |
| 9,867,941 B2 | 1/2018 | McLoughlin et al. |
| 9,878,092 B2 | 1/2018 | McLoughlin et al. |
| 9,884,152 B2 | 2/2018 | McLoughlin et al. |
| 9,901,673 B2 | 2/2018 | McLoughlin et al. |
| 9,901,674 B2 | 2/2018 | McLoughlin et al. |
| 9,901,686 B2 | 2/2018 | Morgan et al. |
| 10,099,013 B2 | 10/2018 | McLoughlin et al. |
| 10,258,740 B2 | 4/2019 | McLoughlin et al. |
| 10,342,925 B2 | 7/2019 | McLoughlin et al. |
| 10,500,341 B2 | 12/2019 | McLoughlin et al. |
| 2006/0129173 A1* | 6/2006 | Wilkinson ........... A61B 5/1513 606/181 |
| 2011/0144594 A1 | 6/2011 | Sund et al. |
| 2012/0191047 A1 | 7/2012 | Raday et al. |
| 2015/0141931 A1 | 5/2015 | McLoughlin et al. |
| 2015/0174340 A1 | 6/2015 | Torris et al. |
| 2016/0325051 A1* | 11/2016 | Keim ..................... A61M 5/20 |
| 2017/0014578 A1* | 1/2017 | Bunch ................. A61M 5/3213 |
| 2017/0239419 A1 | 8/2017 | McLoughlin et al. |
| 2018/0043097 A1 | 2/2018 | Mcloughlin et al. |
| 2018/0071462 A1 | 3/2018 | Morgan et al. |
| 2018/0093041 A1 | 4/2018 | Mcloughlin et al. |

FOREIGN PATENT DOCUMENTS

| | | |
|---|---|---|
| EP | 3 320 932 A1 | 5/2018 |
| WO | 2017/004345 A1 | 1/2017 |

OTHER PUBLICATIONS

AliMed®, "Long-Term Care & Home Health Care Supplies—AliMed", <https://www.alimed.com/nursing-home-supplies/>, accessed Sep. 16, 2019, 4 pages.

Bespak, "Syrina™", <https://web.archive.org/web/20160316221015/http://www.bespak.com/devices-technologies/injectables/syrina/>, accessed Jan. 4, 2018, 8 pages.

AliMed®, "Carrot™ Hand Contracture Orthoses", <https://www.alimed.com/carrot-hand-contracture-orthoses/?ref=carrot-LTC-banner>, accessed Sep. 16, 2019, 6 pages.

Protolabs, "Designing for Moldability: Complex Features", How to mold parts with undercuts and through-holes, <https://www.protolabs.com/resources/white-papers/designing-for-moldability-complex-features/>, accessed Sep. 16, 2019, 5 pages.

Extended European Search Report dated Oct. 29, 2019 in European Application No. 19194858.7 (9 pages).

European Examination Report dated Mar. 2, 2022, in counterpart European Patent Application No. 19194858.7 (5 pages, in English).

* cited by examiner

NEEDLE SHIELD GRIP DEVICES AND RELATED METHODS

CROSS-REFERENCE TO RELATED APPLICATIONS

This patent application claims the benefit of priority under 35 U.S.C. § 119 to U.S. Provisional Patent Application No. 62/734,665, filed Sep. 21, 2018, which is herein incorporated by reference in its entirety.

TECHNICAL FIELD

Aspects of the present disclosure generally relate to medical devices, methods of fabrication, and related procedures. In particular, some aspects of the present disclosure relate to needle shield/guard grip devices, and methods therefor.

BACKGROUND

Needles, e.g., hypodermic needles, are often used in conjunction with a syringe or other such pump for injection of substances into, or extraction of substances from, a body of a patient. For example, needles may be used for the intravenous, subcutaneous, and/or intramuscular injection of substances (e.g., medicaments, dyes, therapeutic agents, visual markers, cellular products, etc.). Additionally, needles may be used for removal of blood (e.g., venipuncture) or other such biological substances from the body. Needles may include a body terminating in a needle tip designed to puncture the skin of the patient. As such, needle tips are commonly sharp and include a pointed and/or beveled end. A lumen may be disposed within the needle body and terminating in an opening in the needle tip. To prevent inadvertent "needle sticks" (e.g., inadvertent insertion of a needle tip into/through skin) or damage to the needle itself, a shield (also referred herein as a "guard") may be placed so as to cover or surround the needle tip until the time of use, and in some cases, be returned following use of the needle. Such shields, however, are often difficult to securely grasp by certain users. For example, such shields are commonly small and are configured in shapes (e.g., cylindrical shapes) that prove difficult for persons with reduced finger dexterity or sensitivity to grasp (e.g., as a result of comorbidity of osteoarthritis in the hand).

SUMMARY

Aspects of the present disclosure relate to, among other things, systems, devices, and methods relating to needle shield/guard grip assemblies, and methods therefor, as described in greater detail below. Each of the aspects disclosed herein may include one or more of the features described in connection with any of the other disclosed aspects.

In one example, a needle guard grip device may include a body extending from a first end to a second end along a central longitudinal axis of the body. The body may include a plurality of ribs extending perpendicularly to the central longitudinal axis. The plurality of ribs may include a first set of longitudinally spaced ribs disposed on a first side of the central longitudinal axis, and a second set of longitudinally spaced ribs disposed on a second side of the central longitudinal axis that is opposite of the first side. Moving along the central longitudinal axis, ribs of the first set of longitudinally spaced ribs may alternate with ribs of the second set of longitudinally spaced ribs. The body may include an interior cavity extending from an opening in the first end of the body to a wall extending perpendicularly to the central longitudinal axis. One rib of the plurality of ribs may be positioned closer to the second end of the body than the wall. A first rib of the first set of longitudinally spaced ribs may include a convex external surface, and a second rib of the first set of longitudinal spaced ribs may include a concave external surface. Additionally, a retainer may be disposed within the interior cavity and may have a tab extending from a portion of the retainer closest to the first end of the body. The tab may extend toward the central longitudinal axis and at an angle to the central longitudinal axis.

Examples of the needle guard grip device may include one or more of the following features. Adjacent ribs of the plurality of ribs may be separated from one another by an opening into the body. The first rib may be positioned closer to the first end of the body than the second end of the body. The second rib may be positioned closer to the second end of the body than the first end of the body. The first rib may be one rib of a first group of ribs that include convex external surfaces. The second rib may be one rib of a second group of ribs that include concave external surfaces. Each rib of the plurality of ribs may extend from a first side wall of the body to a second side wall of the body. The retainer may be a clip having an opposing pair of arms, and each arm of the opposing pair of arms may extend at an angle relative to the central longitudinal axis of the body. The retainer may be positioned entirely within the interior cavity of the body. The retainer may be a clip having an opposing pair of arms connected together by a planar surface extending perpendicularly to the central longitudinal axis.

In a further example, a needle guard grip device may include a body extending from a first end to a second end along a central longitudinal axis of the body. The body may include a plurality of ribs. A first group of ribs of the plurality of ribs may have convex external surfaces and a second group of ribs of the plurality of ribs may have concave external surfaces. The body may include an interior cavity extending from an opening in the first end of the body to a wall extending perpendicularly to the central longitudinal axis of the body. Additionally, a clip may be disposed within the interior cavity. The clip may include a planar surface extending perpendicularly to the central longitudinal axis, a pair of arms depending from the planar surface and extending towards the first end of the body. A first arm of the pair of arms may include a tab extending away from the first arm and toward the central longitudinal axis.

Examples of the needle guard grip device may include one or more of the following features. Each arm of the pair of arms may extend towards the first end of the body at an angle to the central longitudinal axis. A rib of the plurality of ribs may lie in a plane perpendicular to the central longitudinal axis. The tab may extend toward the second end of the body at an angle to the central longitudinal axis. The first end of the body may have a first cross-sectional dimension and the second end of the body may have a second cross-sectional dimension larger than the first cross-sectional dimension.

In a further example, a method of fabricating a needle guard grip device may include molding a body. The body may include a first end, a second end, an interior cavity extending from an opening in the first end towards the second end along a central longitudinal axis of the body, and a plurality of ribs positioned between the first and second ends. The method may further include positioning a clip within the interior cavity of the body. The clip may include a planar surface, a first arm depending from the planar surface and extending towards the first end of the body, a second arm depending from the planar surface and extending towards the first end of the body, a first tab extending from the first arm, and a second tab extending from the second arm.

Examples of the method may further include one or more of the following features. Each rib of the plurality of ribs may extend perpendicularly to the central longitudinal axis of the body. The first tab and the second tab may extend toward the second end of the body. The first tab and the second tab may extend toward the central longitudinal axis of the body. A first group of ribs of the plurality of ribs may have convex external surfaces, and a second group of ribs of the plurality of ribs may have concave external surfaces.

In a further example, a needle guard grip assembly may include a body having a first end, a second end, a longitudinal axis, a plurality of ribs, and an interior cavity that extends from an opening at the first end toward a wall adjacent the second end. The interior cavity may be configured to receive a needle shield therein. Additionally, a clip may be disposed within the interior cavity of the body. The clip may include a tab extending into the interior cavity and configured to contact the needle shield. The tab may extend from a portion of the clip adjacent to the first end of the body, radially inward and toward the second end of the body at an angle with respect to the longitudinal axis of the body.

Examples of the needle guard grip assembly may include one or more of the following features. A rib of the plurality of ribs may lie in a plane that is perpendicular to the longitudinal axis of the body. A rib of the plurality of ribs may include a portion deflected radially inwardly toward the longitudinal axis of the body. The wall may lie in a plane that is perpendicular to the longitudinal axis of the body. The first end of the body may have a first cross-sectional dimension and the second end of the body may have a second cross-sectional dimension larger than the first cross-sectional dimension.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−10% of a stated value. Moreover, in the claims, values, limits, and/or ranges of, for example, the described devices, means the recited value, limit, and/or range ±10%.

BRIEF DESCRIPTION OF THE DRAWINGS

The accompanying drawings, which are incorporated in and constitute a part of this specification, illustrate exemplary aspects that, together with the written descriptions, serve to explain the principles of this disclosure.

DETAILED DESCRIPTION

Examples of the present disclosure relate to needle shield/guard grip devices, related assemblies, and methods of fabrication and use thereof. The needle shield/guard grip devices may be positioned so as to cover a needle tip and needle guard/shield, thereby facilitating safe and secure handling of the needle to avoid inadvertent needle sticks, reducing risks of injury, contamination, and damage to the needle itself, as well as facilitating remove of the needle shield/guard for use when appropriate.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative and directional positions of the components of an exemplary needle guard grip device. When used herein, "proximal" refers to a position closer to the exterior of the body of the patient or closer to a user/operator and/or medical professional using the needle. In contrast, "distal" refers to a position farther away from the user/operator and/or medical professional using the needle, or closer to the needle tip for insertion into the interior of the body of the patient. The terms "needle guard" and "needle shield" are used interchangeably in this disclosure.

Figure 1:
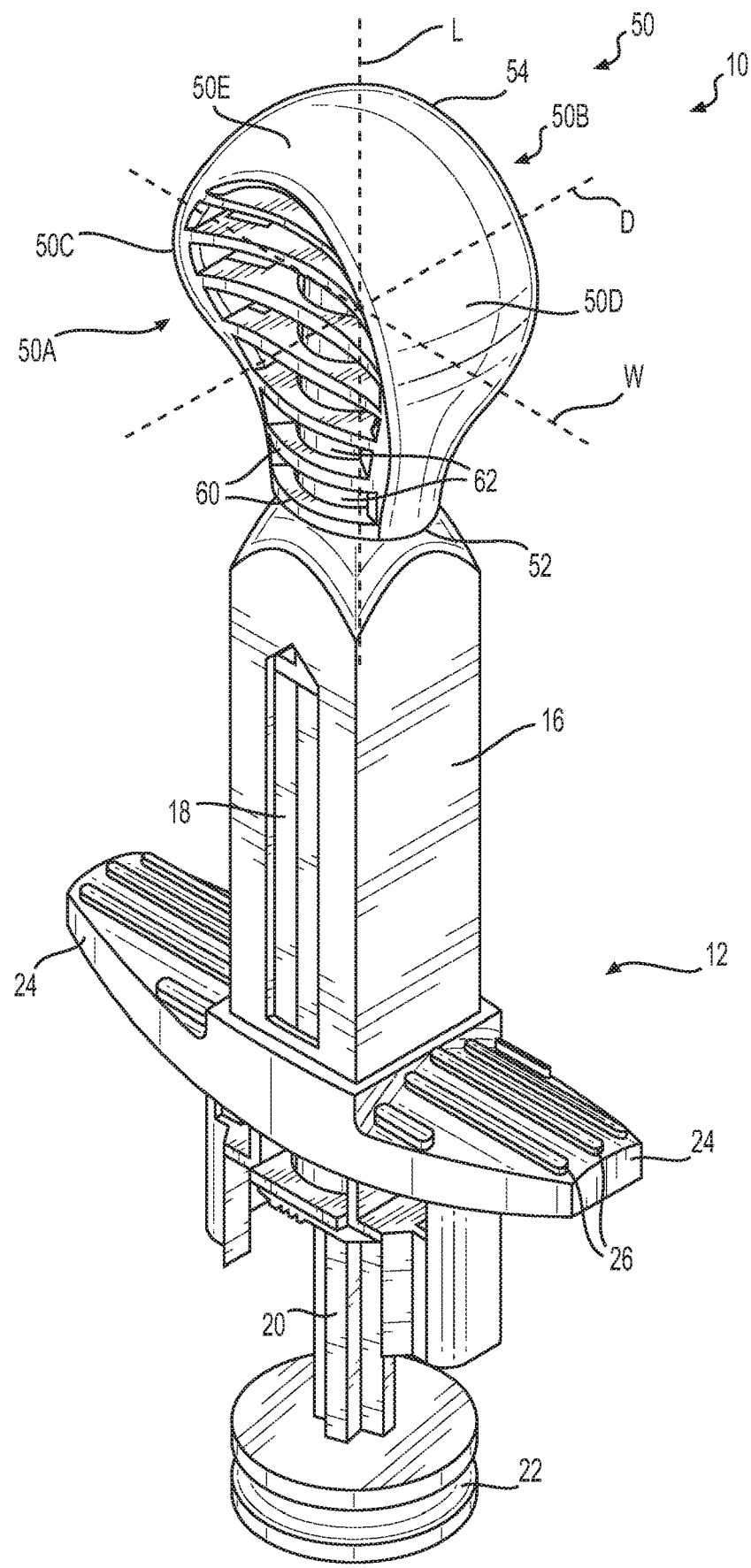
FIG. 1 illustrates an exemplary needle shield/guard grip device coupled to a syringe, according to an aspect of the present disclosure.
Figure 2:
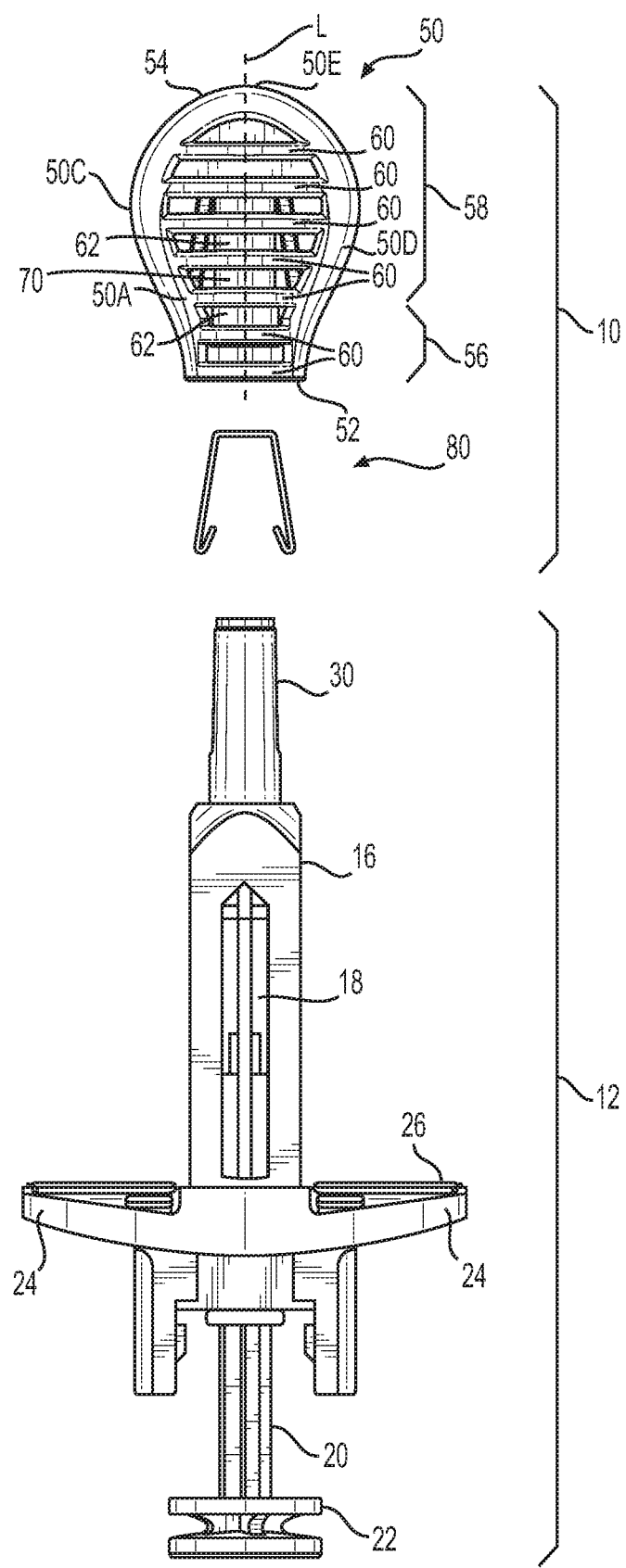
FIG. 2 illustrates an exploded view of the needle shield/guard grip device and syringe of FIG. 1.
Figure 4:
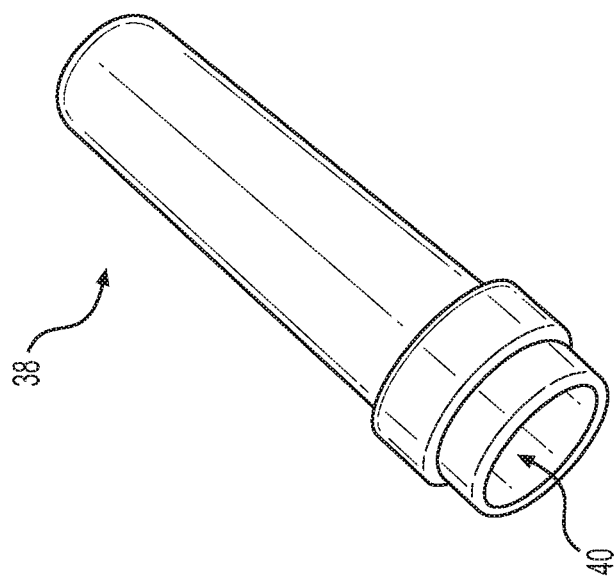
FIG. 4 is a perspective view of an exemplary soft needle shield of the shield/guard grip device of FIG. 1.
Figure 8:
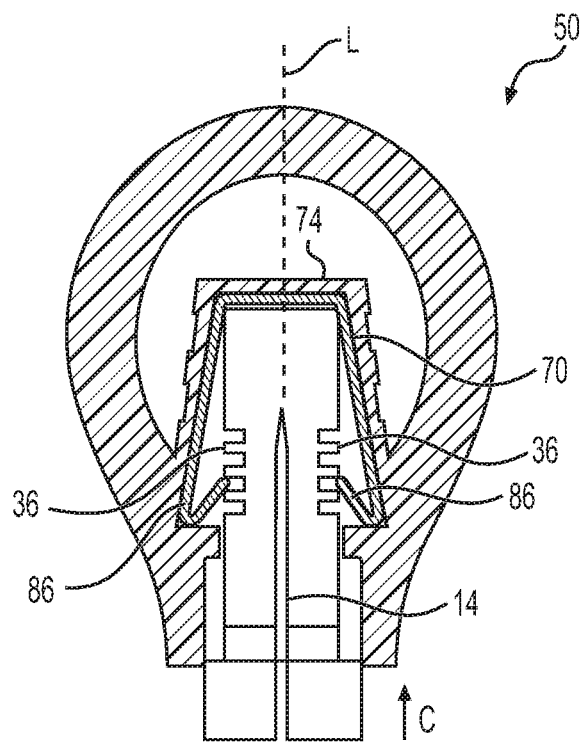

FIGS. 1 and 2 illustrate an exemplary medical device including a grip device 10 coupled to an exemplary syringe 12 having a needle 14 (FIG. 8). While references herein refer to syringe 12, it is understood that the disclosure is not so limited. Rather, grip device 10 may be coupled to any appropriate injection device having a needle 14 such as, e.g., a pump, an autoinjector, and/or an intravenous catheter (e.g., for use with an intravenous line (IV)), etc. By way of example only, syringe 12 may include a housing 16 defining a chamber 18 therein. Chamber 18 may be a barrel that is fluidly coupled with needle 14. At least a portion of a plunger rod 20 may be movably (e.g., slidably) received within chamber 18 such that, upon actuation of plunger rod 20 in a first (e.g., distal) direction, substances within chamber 18 are expelled through needle 14. Additionally, upon actuation of plunger rod 20 in a second (e.g., proximal) direction, opposite the first direction, substances may be drawn into needle 14 (e.g., via negative pressure). Plunger rod 20 may be actuated, for example, by advancing or retracting plunger rod 20 relative to housing 16. For example, a user may place their thumb or a finger on a flange, extension, or end 22 of plunger rod 20 while wrapping one or more additional fingers around one or more wing(s) 24 (e.g., flanges or protrusions extending radially outwardly of housing 16). To actuate plunger rod 20 in the first direction, a user may compress or squeeze end 22 toward wing(s) 24, or vice versa. To actuate plunger rod 20 in the second direction, a user may pull end 22 away from wing(s) 24, or vice versa. Optionally, wings 24 and/or end 22 may include one or more baffles, ribs, protrusions, and/or textured or raised elements 26 to facilitate secure gripping by the user. As those with ordinary skill in the art will understand, grip device 10 may be removed, thereby exposing needle 14, prior to actuation of plunger rod 20.

Turning now to FIG. 2, syringe 12 may include a needle shield 30. Shield 30 may be arranged to as to surround or cover needle 14 (shown in FIG. 8) to avoid damage to needle 14, maintain sterility of needle 14, and/or avoid unintentional "needle sticks" prior to use. Further details of needle shield 30 will be discussed below in connection with FIG. 8. Grip device 10 may include a grip body 50 configured to be secured to shield 30 via any suitable method. Those of ordinary skill in the art will readily recognize that grip device 10 may be mechanically secured to shield 30 by, e.g., a suitable adhesive or other mechanical engagement, such as, e.g., retainer 80. Further details of retainer 80 will be described in connection with FIG. 14. As shown in FIGS. 1 and 2, grip body 50 defines, includes, or has one or more ribs 60 extending along body 50, as will be described in further detail below.

Figure 3:
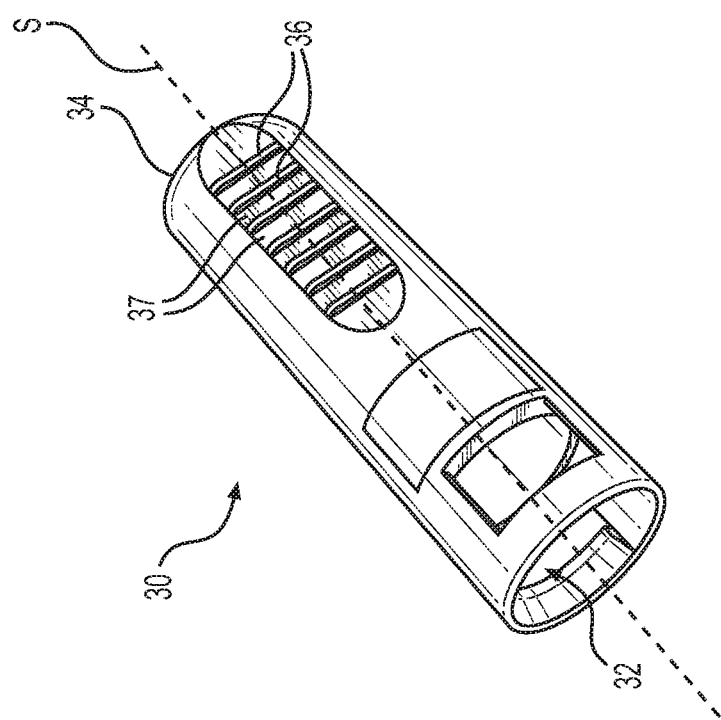
FIG. 3 is a perspective view of an exemplary rigid needle shield of the needle shield/guard grip device of FIG. 1.

FIG. 3 illustrates a perspective view of needle shield 30. Needle shield 30 may define a cavity 32 within which needle 14 may be received. As such, needle shield 30 covers or surrounds needle 14 (not shown in FIG. 3), thereby preventing contamination, inadvertent "needle sticks," or damage to needle 14 itself. To that end, distal end 34 of needle shield 30 may be closed or covered. Additionally, needle shield 30 may include one or more ridges, teeth, raised textural portions, or protrusions 36. Adjacent to each protrusion 36 may be a recess 37. As shown, for example, the one or more protrusions 36 may extend generally orthogonal to a longitudinal axis S of needle shield 30. In use, retainer 80 (not shown in FIG. 3) may interact with the one or more protrusions 36 or recesses 37 so as to grip or secure grip body 50 (not shown in FIG. 3) to needle shield 30, as will be described in further detail below. While protrusions 36 are depicted as extending generally orthogonally to a longitudinal axis of needle shield 30, the disclosure is not so limited. Rather, in some exemplary arrangements, protrusions 36 may be angled relative to the longitudinal axis of needle shield 30 at any angle other than 90°. Additionally, while protrusions 36 are depicted as extending along a straight line along only a portion of the perimeter of needle shield 30, in other arrangements, protrusions 36 may be curved and/or extend about the entirety of the perimeter of needle shield 30. Needle shield 30 may be comprised of one or more thermoplastic materials such as, for example, polypropylene, polycarbonate, acrylonitrile butadiene styrene, or combinations thereof. Optionally, a soft needle shield or inner needle shield 38 may be received within cavity 32 of needle shield 30, while needle 14 (FIG. 8) is received within a cavity 40 of inner needle shield 38. Inner needle shield 38 may comprise a generally compressible material such as, e.g., thermoplastic elastomer, thermoplastic polyurethane, isoprene, or combinations thereof. Soft needle shield 38 may cushion needle 14 so as to further prevent contamination, inadvertent "needle sticks," or damage to needle 14 itself.

FIGS. 5-8 illustrate the assembly of an exemplary retainer 80 (FIG. 14), needle shield 30, and needle 14 within grip body 50 of FIG. 1. To that end, and as described in further detail below, grip body 50 may include an interior cavity 70. Interior cavity 70 may extend from an opening 72 to a cavity wall 74 extending perpendicular to longitudinal axis L of grip body 50. A pair of walls 76 may depend from respective ends of cavity wall 74. As shown, each wall 76 of the pair of walls 76 may extend at a non-right angle relative to longitudinal axis L such that cavity wall 74 and pair of walls 76 collectively define interior cavity 70 having a substantially inverted "U" shape. Alternatively, interior cavity 70 may have any shape appropriate so as to cooperate with retainer 80 (or other suitable mechanical fastener) to couple grip body 50 to shield 30, as will be described in further detail below.

As shown, opening 72 may have a first width dimension. In one arrangement, the first width dimension may be about 8.6 mm. Additionally, grip body 50 may include a constriction 73 having a second width dimension smaller than the first width dimension. In one arrangement, the second width dimension may be about 7.6 mm. A ledge or shoulder 77 may extend between an end of each wall 76 of the pair of walls 76 and constriction 73. An outermost width dimension of shoulder 77 may be about 11.87 mm. It is understood that any one or more of the edges of grip body 50 defining opening 72, constriction 73, and shoulder 77 may be chamfered or otherwise rounded. Once assembled, one or more portions of retainer 80 may be seated or rest on shoulder 77.

Figure 6:
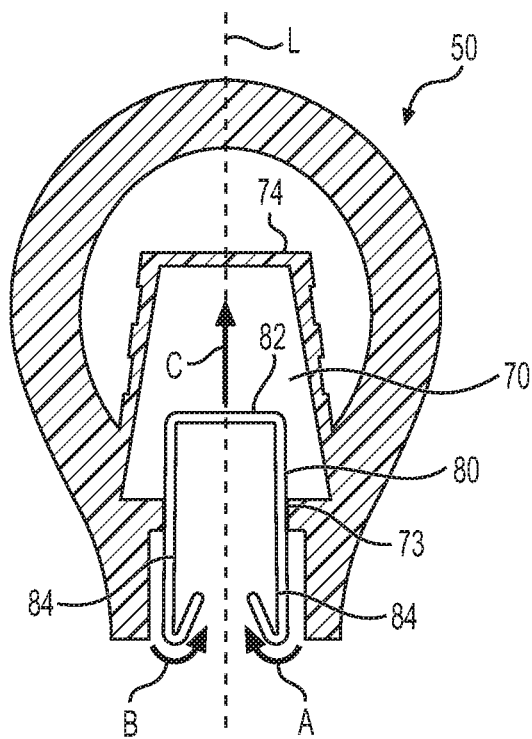
Figure 7:
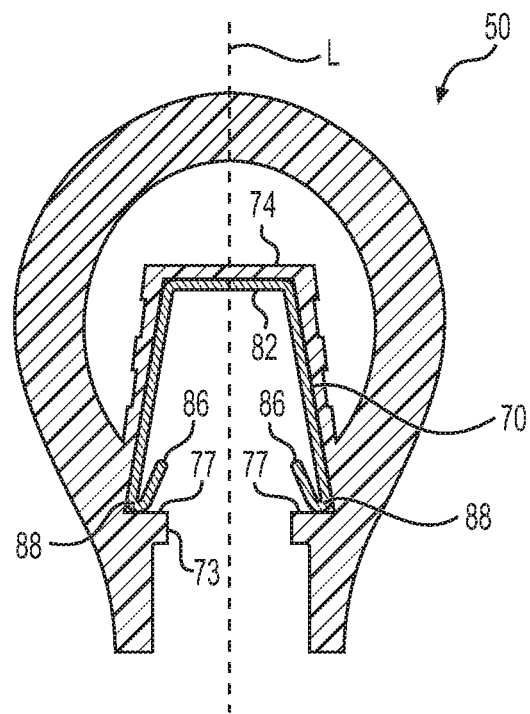

Turning now to FIG. 6, in order to insert retainer 80 within cavity 70, retainer 80 must pass through constriction 73. However, retainer 80 may include at least a portion (e.g., arms 84) having a width dimension greater than the second width dimension of constriction 73, as will be described in further detail below. Accordingly, in order to insert retainer 80 within cavity 70, one or more portions of retainer 80 (e.g., arms 84) may be urged, bent, or otherwise deflected radially inwardly, e.g., toward longitudinal axis L of grip body 50. For example, a first arm 84 may be deflected in a first direction A toward longitudinal axis L and/or a second arm 84 may be deflected in a second direction B toward longitudinal axis L so as to reduce the width dimension of retainer 80. Once so compressed, retainer 80 may be advanced in the direction C along longitudinal axis L into cavity 70, until one or more portions of retainer 80 (e.g., base 82) may abut or otherwise contact cavity wall 74, as shown in FIG. 7.

Figure 14:
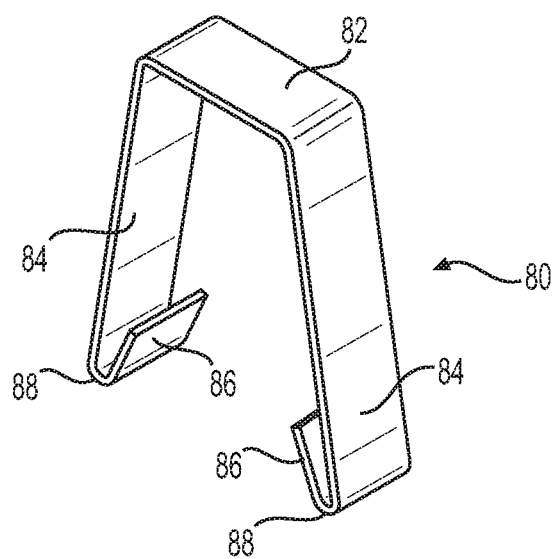
FIG. 14 illustrates an exemplary retainer device, according to an aspect of the present disclosure.

Once so positioned, retainer 80 may be permitted to expand (e.g., any compressive force applied to arms 84 may be released) such that retainer 80 may return to a non-compressed state (e.g., as shown in FIG. 14). Upon expansion of retainer 80, one or more portions (e.g., bends 88) of retainer 80 may be seated or rest on shoulder 77, while a flap or tab 86 of each arm 84 may extend radially inwardly towards longitudinal axis L and into interior cavity 70. Further details of retainer 80 will be described below in connection with FIG. 14.

Next, needle 14, received within needle shield 30, may be advanced into interior cavity 70 of grip body 50. That is, needle 14 and shield 30 may be advanced in the direction C along the longitudinal axis L of grip body 50 until tabs 86 of retainer 80 contact protrusions 36 of shield 30. As such, tabs 86 are "caught" or retained by protrusions 36 or recesses 37 of shield 30. One such method for advancing needle shield 30 and needle 14 into grip body 50 may be via a vertical Schmidt press (not shown). For instance, the press may be loaded with a nest or housing within which grip body 50 and syringe 12 are arranged. Next, grip body 50 and/or syringe 12 may be advanced toward each other via the press so as to insert shield 30 into interior cavity 70 of grip body 50. In addition, one or more sensors (e.g., pressure sensor, load cell, displacement sensors) may be positioned on the press and in communication with a display device (e.g., a monitor, not shown). The sensors may be arranged to measure a load imparted on grip body 50 or syringe 12. If the load exceeds a pre-determined threshold, the sensors may communicate with the monitor to deliver a "fail" signal. If, however, the sensed load is within an acceptable range of the load, the sensors may communicate with the monitor to deliver a "pass" signal. In such a manner, a manufacturer may readily observe whether the assembled device is satisfactory. In addition, following pressing of the components together, a rod may be activated so as to eject the assembly from the nest or housing for removal by an operator.

When a user determines a need or desire to inject or remove a substance via needle 14, he or she may grasp grip body 50 and apply a force in the direction C (FIG. 6) along longitudinal axis L (e.g., a tensioning or pulling force) away from syringe 12. Upon application of the tensioning or pulling force, retainer 80, positioned within internal cavity 70 of grip body 50 and contacting protrusions 36 or recesses 37 of shield 30, will impart a likewise force on shield 30. That is, as grip body 50 is removed from needle 12, so too will shield 30 be removed from needle 14.

Figure 10:
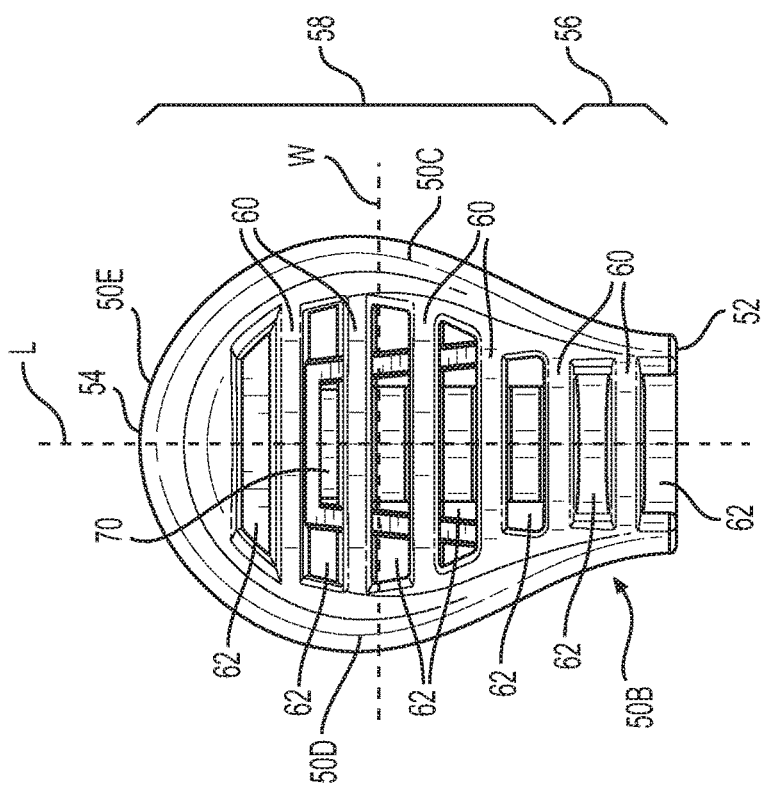
FIG. 10 illustrates a back-view of the exemplary needle shield/guard grip device of FIG. 1.
Figure 9:
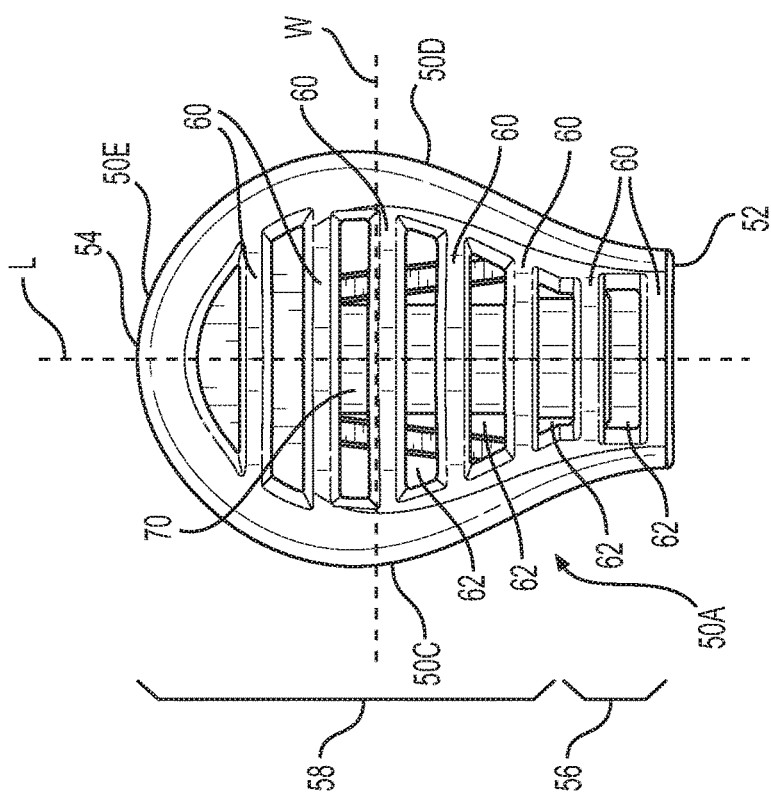
FIG. 9 illustrates a front-view of the exemplary needle shield/guard grip device of FIG. 1.
Figure 11:
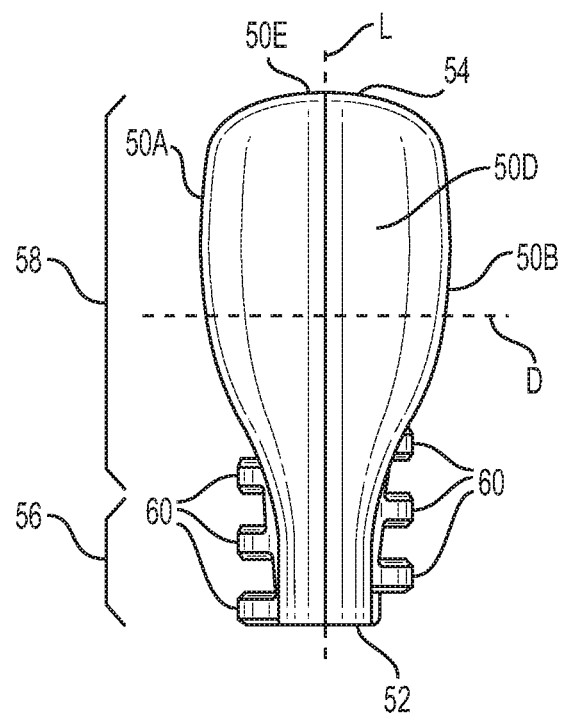
FIG. 11 illustrates a side-view of the exemplary needle shield/guard grip device of FIG. 1.

As shown in FIGS. 1, 2, and 5-11, grip body 50 (or body 50) may have a height or length extending along longitudinal axis L between a first (e.g. proximal) end 52 to a second (e.g., distal) end 54. In some arrangements, the length of grip body 50 may be between about 30 mm and about 40 mm, or about 33.74 mm. Additionally, grip body 50 may have a width extending along a width axis W (FIGS. 9, 10, and 13), orthogonal to longitudinal axis L. As shown, the width of grip body 50 may vary along the length of grip body 50. For example, grip body 50 may include a neck portion 56 and a head portion 58 (FIGS. 9, 10, and 11). As shown, the widest or largest width dimension of neck portion 56 may be smaller or less than the widest or largest width dimension of head portion 58. In some arrangements, the widest or largest width dimension of the head portion 58 (or grip body 50 as a whole) may be between about 20 mm and about 30 mm, or about 26.19 mm. Moreover, grip body 50 may have a thickness extending along a depth axis D (FIGS. 11 and 13), orthogonal to longitudinal axis L and width axis W. The depth of grip body 50 may vary along the length of grip body 50. As shown, for example, the thickest or largest depth dimension of neck portion 56 may be smaller or less than the thickest or largest depth dimension of head portion 58 (FIGS. 1 and 11). In some arrangements, the thickest or largest depth dimension of head portion 58 (or grip body 50 as a whole) may be between about 10 mm and about 20 mm, or about 15.75 mm. In other words, grip body 50 defines a generally bulbous shape having a relatively smaller neck portion 56 than head portion 58, and having a first (or front) face 50A, a second (or rear) face 50B, a pair of lateral (or side) surfaces 50C, 50D, and a rounded or arcuate top surface 50E, monolithically formed as a one-piece molded construction. As shown in FIG. 1, surfaces 50C, 50D, and 50E together may form a single, continuous or smooth, surface that forms a peripheral surface of grip body 50.

With continuing reference to FIG. 1, grip body 50 defines, includes, or is made of a plurality of ribs 60. Ribs 60 may be arranged along grip body 50 in any appropriate manner. For example, each rib 60 may extend orthogonally or perpendicular to the longitudinal axis L of grip body 50, as show in FIGS. 1, 2, 9, and 10. In other arrangements, however, one or more ribs 60 may extend along or parallel with longitudinal axis L, or may be angled at a non-right angle relative to longitudinal axis L of grip body 50 without departing from the scope of this disclosure. As shown in FIG. 9, for example, first face 50A of grip body 50 may include a plurality of ribs 60 extending generally perpendicular to the longitudinal axis L of grip body 50. By way of example only, first face 50A may include or define seven ribs 60 spanning a width of first face 50A. It is understood, however, that the described quantity of ribs 60 is merely exemplary, and in other arrangements, first face 50A of body 50 may include, define, or be made of more or less ribs 60 without departing from the scope of this disclosure. As shown, a proximalmost rib 60 of the ribs 60 of first face 50A may be positioned at, or coplanar with, first end 52 of grip body 50. Further, each additional rib 60 of first face 50A may be spaced from one or more adjacent ribs 60 along the grip body 50. While ribs 60 are shown equidistantly spaced, the disclosure is not so limited. For example, at least one or some of ribs 60 of first face 50A may be non-equidistantly spaced from an adjacent rib 60.

Additionally, as shown in FIG. 10 for example, second face 50B of grip body 50 may include, define, or be made of a plurality of ribs 60 extending generally perpendicular to the longitudinal axis L of grip body 50. By way of example only, second face 50B may include or define six ribs 60 spanning a width of second face 50B. It is understood, however, that the described quantity of ribs 60 is merely exemplary, and in other arrangements, second face 50B of body 50 may include, define, or be made of more or less ribs 60 without departing from the scope of this disclosure. As shown, a proximalmost rib 60 of the ribs 60 of second face 50B may be spaced away (e.g., closer to second end 54) from first end 52 of grip body 50. Further, each additional rib 60 of second face 50B is spaced from one or more adjacent ribs 60 along the grip body 50. While ribs 60 are shown equidistantly spaced, the disclosure is not so limited. For example, at least one or some of ribs 60 of second face 50B may be non-equidistantly spaced from an adjacent rib 60.

With reference now to FIGS. 1, 9, and 10, openings or spaces 62 between adjacent ribs 60 of first face 50A and openings or spaces 62 between adjacent ribs 60 of second face 50B extend through the entirety of a first face 50A and second face 50B, respectively. That is, first face 50A and second face 50B may include a plurality of spaces 62 between adjacent ribs 60, at least some of which may communicate between interior cavity 70 of grip body 50 and surrounding atmosphere. Alternatively, such spaces 62 may not extend through the entire of the thickness of first face 50A and/or second face 50B. Rather, such spaces 62 may comprise recesses or detents that do not permit communication between interior cavity 70 and atmosphere. Additionally, in some arrangements, only some of spaces 62 between adjacent ribs 60 of either or both the first face 50A and/or the second face 50B extend entirely through the thickness of the respective first 50A or second face 50B. In some arrangements, spaces 62 between adjacent ribs 60 may have a height in the direction of longitudinal axis L that is substantially equal to the height of one or more ribs 60 in the direction of longitudinal axis L. In other arrangements, spaces 62 may have a height in the direction of longitudinal axis L that is greater than or less than the height of one or more ribs 60. Further, in some arrangements, at least one rib 60 or space 62 may have a height in the direction of the longitudinal axis that is different than the height of at least one other rib 60 or space 62.

As shown in FIG. 11, ribs 60 of first face 50A may be offset relative to ribs 60 of second face 50B along longitudinal axis L. That is, proximalmost rib 60 of second face 50B may be positioned between proximalmost rib 60 of first face 50A and the second most proximal rib 60 (i.e., the longitudinally adjacent rib 60) of first face 50A. That is, ribs 60 of first face 50A and the ribs 60 of the second face 50B may be alternatingly arranged along grip body 50. In other words, moving along the longitudinal axis L, ribs 60 of the first face 50A (e.g., a first set or ribs 60) may alternate with ribs 60 of the second face 50B (e.g., a second set of ribs 60). Alternatively, in some arrangements, plural (e.g., two) ribs 60 of one of first face 50A and second face 50B may be positioned between adjacent ribs of the other of first face 50A and second face 50B. While first face 50A and second face 50B are illustrated and described as having a different number of ribs 60, the disclosure is not so limited. Rather, in some arrangements, each of first face 50A and second face 50B may include a common number of ribs 60, without departing from the scope of the present disclosure.

Figure 5:
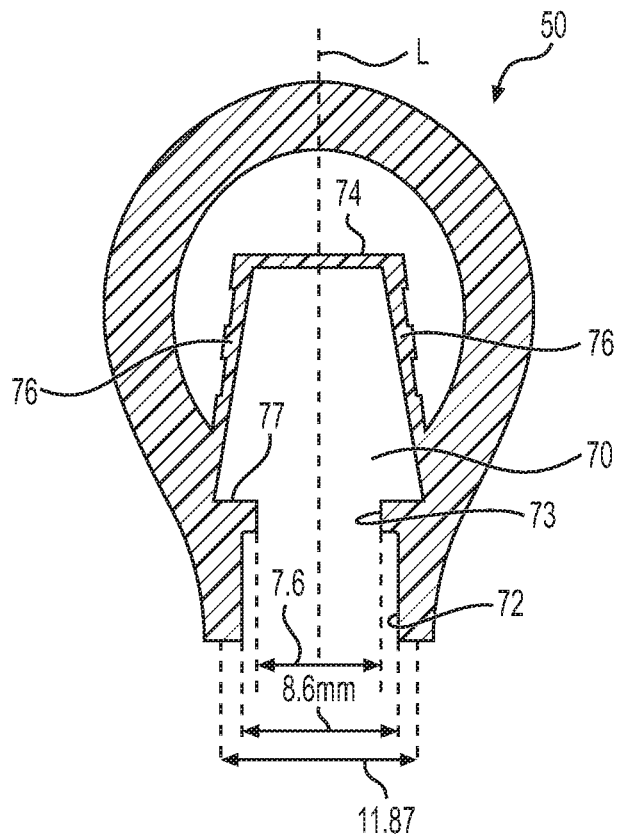
FIGS. 5-8 illustrate the assembly of an exemplary retainer, needle shield, and needle within the needle shield/guard grip device of FIG. 1.

Additionally, at least some of ribs 60 of first face 50A and/or second face 50B may be deflected radially outwardly away from longitudinal axis L of grip body 50, as shown in, for example, FIGS. 1 and 5. Indeed, by way of example only, the proximalmost three ribs 60 positioned on each of first face 50A and second face 50B may include a portion (e.g., at least a central portion thereof) deflected radially outwardly of (e.g., away from) longitudinal axis L of grip body 50. As shown in FIG. 1, the three proximalmost ribs 60 may include a substantially convex configuration. That is, at least a portion (e.g., central portion) of such ribs 60 may extend farther away from longitudinal axis L than at least another portion (e.g., a portion where rib 60 meets or merges with one of lateral (or side) surfaces 50C or 50D). In other embodiments, however, these ribs 60 may include a substantially concave or planar configuration. In other arrangements more or less ribs 60 of first face 50A and/or second face 50B may be deflected radially outwardly.

Additionally, at least some of ribs 60 of first face 50A and/or second face 50B may be deflected radially inwardly toward longitudinal axis L of grip body 50, as shown in, for example, FIG. 1. Indeed, by way of example only, ribs 60 positioned distally of the proximalmost three ribs 60 positioned on each of first face 50A and/or second face 50B may include a portion (e.g., at least a central portion thereof) deflected radially inwardly toward longitudinal axis L of grip body 50. As shown in FIG. 1, the ribs 60 positioned distally of the three proximalmost ribs 60 may include a substantially concave configuration. That is, at least a portion (e.g., central portion) of such ribs 60 may extend farther inwardly toward longitudinal axis L than at least another portion (e.g., a portion where rib 60 meets or merges with one of lateral (or side) surfaces 50C or 50D). In other embodiments, however, these ribs 60 may include a substantially convex or planar configuration. In other arrangements more or less ribs 60 of first face 50A and/or second face 50B may be deflected radially inwardly.

While radially outwardly and radially inwardly deflected ribs 60, described above, are illustrated as curved, rounded, or otherwise arcuate in FIG. 1, the disclosure is not so limited. Rather, any one or more such ribs 60, be it deflected radially inwardly or radially outwardly, may include any other shape. For example, such ribs 60 may include one or more planar surfaces.

As noted above, grip body 50 may define an interior cavity 70 extending from opening 72 through first end 52 and towards second end 54 of grip body 50. Additionally, cavity wall 74 may be positioned between first end 52 and second end 54, and in some cases, may be closer to second end 54 than first end 52 of grip body 50. Further, at least one rib 60 is positioned closer to second end 54 than cavity wall 74.

Figure 12:
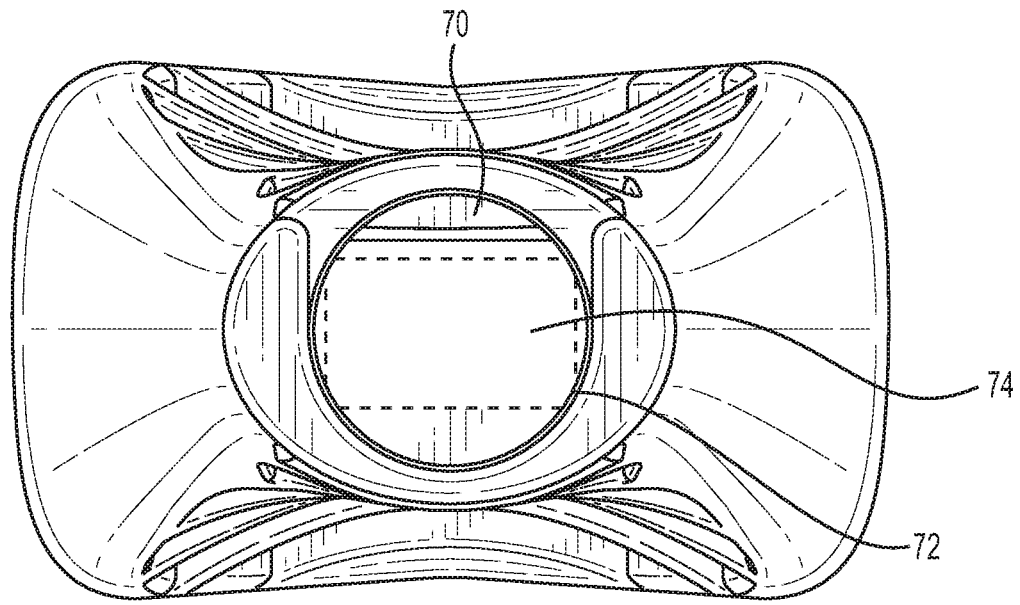
FIG. 12 illustrates a bottom-view of the exemplary needle shield/guard grip device of FIG. 1.
Figure 13:
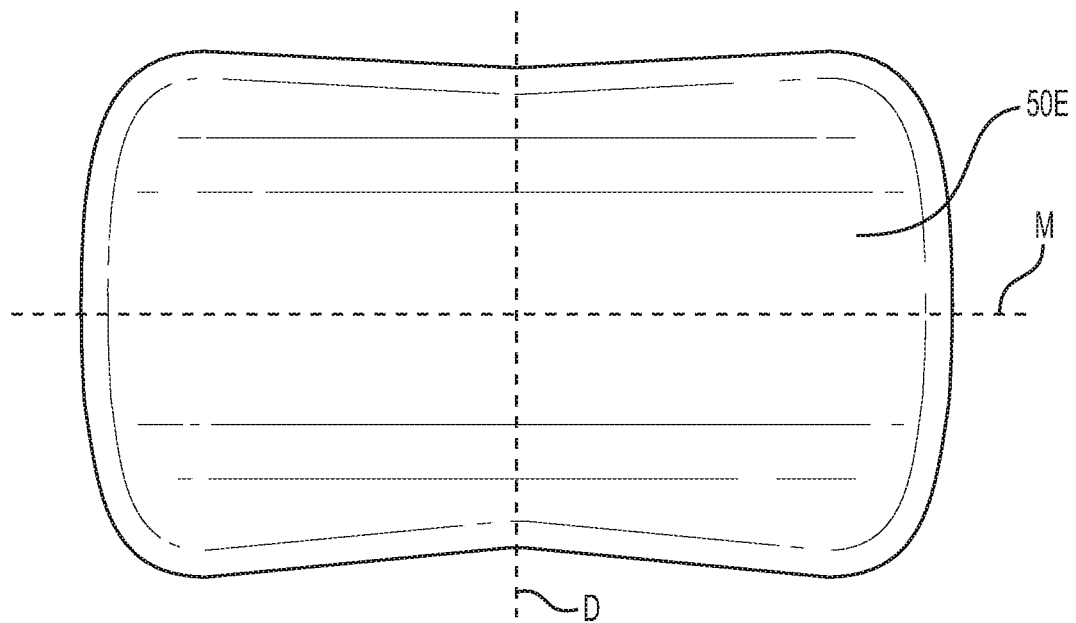
FIG. 13 illustrates a top-view of the exemplary needle shield/guard grip device of FIG. 1.

In other arrangements, however, cavity wall 74 may be positioned closer to first end 52 than second end 54 of grip body 50 or may be angled at a non-right angle relative to longitudinal axis L of grip body 50. As discussed above, the pair of walls 76 may depend from an end of cavity wall 74. As discussed above and as shown in FIGS. 5-8, for example, each wall 76 of the pair of walls 76 may extend at a non-right angle relative to longitudinal axis L. In such a manner, cavity wall 74 and pair of walls 76 collectively define interior cavity 70 having a substantially inverted "U" shape. Alternatively, interior cavity 70 may have any shape appropriate so as to cooperate with retainer 80 (or other suitable mechanical fastener) to couple grip body 50 to shield 30. FIG. 12 illustrates a bottom-view of grip body 50, depicting opening 70 into interior cavity 70 within which cavity wall 74 is positioned. FIG. 13 illustrates a top-view of the grip body 50 illustrating top surface 50E.

Grip body 50 may be comprised of any appropriate materials, such as, for example, a thermoplastic polymer such as acrylonitrile butadiene styrene (ABS). As such, grip body 50, including interior cavity 70, may be formed entirely via a molding process, e.g., a single molding process, including, but not limited to, injection molding, die-casting, and/or compression molding. That is, body 50 may be formed without the need for supplemental cutting or carving of interior cavity 70, or spaces 62, thereby reducing manufacturing complexity, time, and/or expense.

As noted above and as shown in FIG. 14, retainer 80 may include base 82 from which one or more arms 84 depend. For example, retainer 80 may be a clip having a pair of diametrically opposed arms 84 depending from opposite ends of a base 82. As shown in FIG. 14, base 82 may be generally rectangular. Alternatively, retainer 80 may include more or less arms 84 depending from base 82, and base 82 may have any appropriate shape. For example, in some arrangements, three, four, five, or more arms 84 may depend from spaced (e.g., equidistantly or nonequidistantly spaced) portions of base 82. In some arrangements, retainer 80 may include a circular or disc-shaped base 82. Optionally, a cylindrical tube or cone (not shown), rather than the depicted planar arms 84, may depend from base 82. Yet further, such a cylindrical tube or cone, or any plurality of interconnected arms 84, need not depend from base 82. That is, in some arrangements, base 82 may be omitted. Regardless of the shape, number, or construction of arm(s) 84, a proximal end of arm(s) 84 may include a flap or tab 86 angled with respect to each arm 84 via a deflection point or bend 88. That is, a proximal end of each arm 84 may include a tab 86 extending radially inwardly towards longitudinal axis L and into interior cavity 70. As shown, each tab 86 may extend at a non-right angle relative to longitudinal axis L (e.g., between about 45° relative to arm(s) 84 and/or relative to longitudinal axis L). That is, one or more of tabs 86 may extend away from a proximal end of each 84 and toward base 82. In other arrangements, however, each tab 86 may extend perpendicularly to longitudinal axis L and/or parallel with cavity wall 74. As noted above, tab(s) 86 may be arranged so as to engage shield 30. Additionally, as noted above in connection with FIGS. 5-8, a distance in the direction of width axis W (of grip body 50, FIG. 10) between bend(s) 88 of arm(s) 84 may be greater than a size (e.g., diameter) of constriction 73. In such a manner, arm(s) 84 may be deflected towards longitudinal axis L (e.g., retainer 80 may be compressed) so as to be passed through opening 72, through constriction 73, and into interior cavity 70. Indeed, as shown in FIG. 7, retainer 80 may be advanced so that base 82 may abut or otherwise contact cavity wall 74, at which point arm(s) 84 may be expanded so as to contact walls 76 and bend(s) 88 may rest on or otherwise contact shoulder 77.

As described in connection with FIGS. 6 and 8, when a user determines a need or desire to inject or remove a substance via needle 14, he or she may grasp grip body 50 and apply a force in the direction C along longitudinal axis L (e.g., a tensioning or pulling force) away from syringe 12. Due to the ergonomic bulbous shape of grip body 50, a user, even one with reduced dexterity, may easily and comfortably grasp grip body 50 via ribs 60. Upon application of the tensioning or pulling force, retainer 80, positioned within internal cavity 70 of grip body 50 and contacting protrusions 36 of shield 30, will impart a likewise force on shield 30. That is, as grip body 50 is removed from needle 12, so too will shield 30 be removed from needle 14 (FIG. 8). In other words, grip body 50 may facilitate ergonomic and secure removal of shield 30 prior to use.

As noted above and shown in FIG. 14, retainer 80 may include base 82 from which two arms 84 depend. In such an arrangement, retainer 80 may be formed from a single sheet of material. For example, retainer 80 as shown in FIG. 14 may be formed by folding a single (e.g., one-piece monolithic) strip of material. That is, the retainer 80 shown in FIG. 14 and including only two arms 84 (as opposed to the arrangement shown in FIG. 24) may be formed without a cutting or stamping step, thereby simplifying manufacture of retainer 80. Additionally, as no further cutting or stamping processes are required, the overall time and cost of manufacture of retainer 80 may be reduced.

Figure 15A:
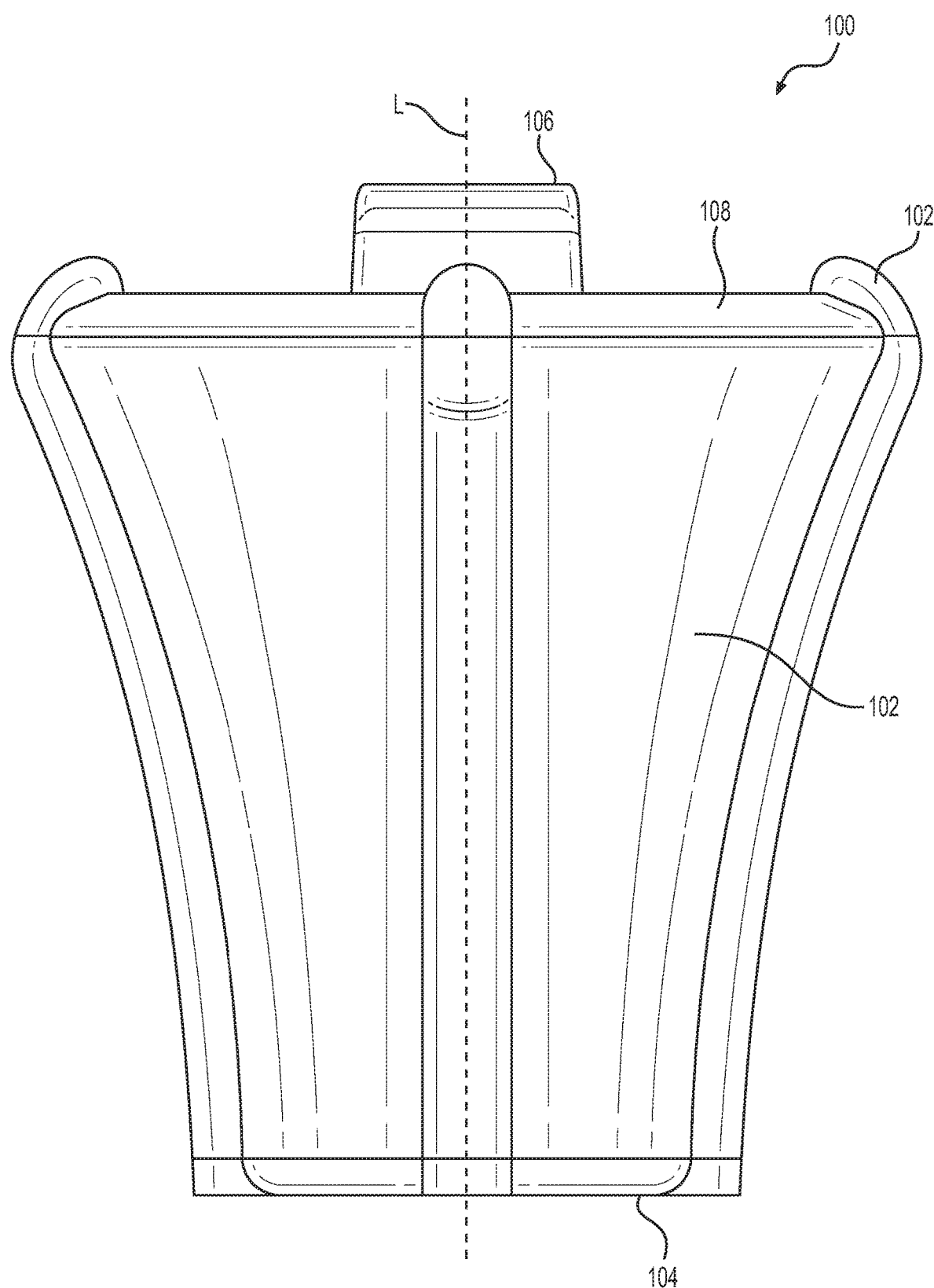
FIG. 15A illustrates another exemplary needle shield/guard grip device, according to a further aspect of the present disclosure.
Figure 15B:
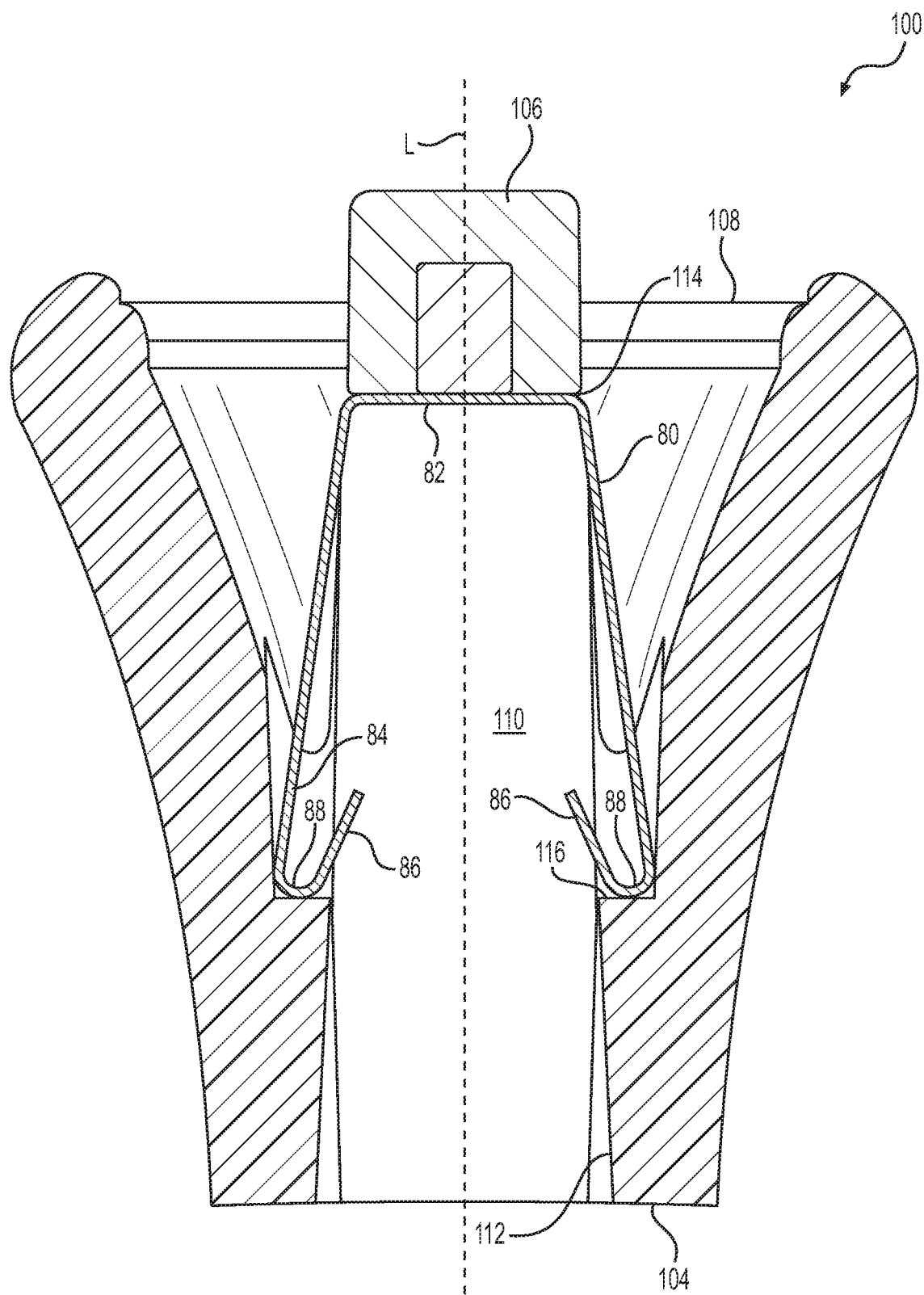
FIG. 15B illustrates a cross-sectional view of the exemplary needle shield/guard grip device of FIG. 15A.

FIGS. 15A and 15B illustrate an exemplary grip body 100, according to a further aspect of the present disclosure. As shown, grip body 100 may be shaped similar to a marker or highlighter cap (e.g., a flared cylinder). Additionally, grip body 100 may include a plurality of ribs 102 or other such grip enhancing features along an exterior surface of grip body 100. For example, grip body 100 may include four such ribs 102 equidistantly spaced about a longitudinal axis L of grip body 100. In other arrangements, grip body 100 may include more or fewer ribs 102, which may either be equidistantly or non-equidistantly spaced about the exterior surface of grip body 100. Additionally, grip body may include a height or length extending along longitudinal axis L between a first end 104 and a second end 106. In some arrangements, second end 106 may be supported via one or more spokes or struts 108. As shown in FIG. 15B, for example, grip body 100 may include an interior cavity 110 extending between an opening 112 at first end 104 and terminating a cavity wall 114 extending perpendicular to longitudinal axis L of grip body 100. As shown, opening 112 may taper (e.g., narrow) in a width dimension (e.g., diameter) toward cavity wall 114. Similar to construction 73 of grip body 50, at least a portion of tapered opening 112 of grip body 100 may have a width dimension smaller than a width dimension of retainer 80. As such, retainer 80 may be received within interior cavity 110 by compressing retainer 80 similar to the manner described above in connection with FIGS. 6 and 7. Once deflected toward a longitudinal axis L of grip body 100, retainer 80 may be passed through opening 112 such that base 82 may abut or otherwise contact cavity wall 114 of grip body 100. Once so positioned, legs 84 may expand such that bends may rest on or otherwise be in contact with shoulder 116.

Figure 16:
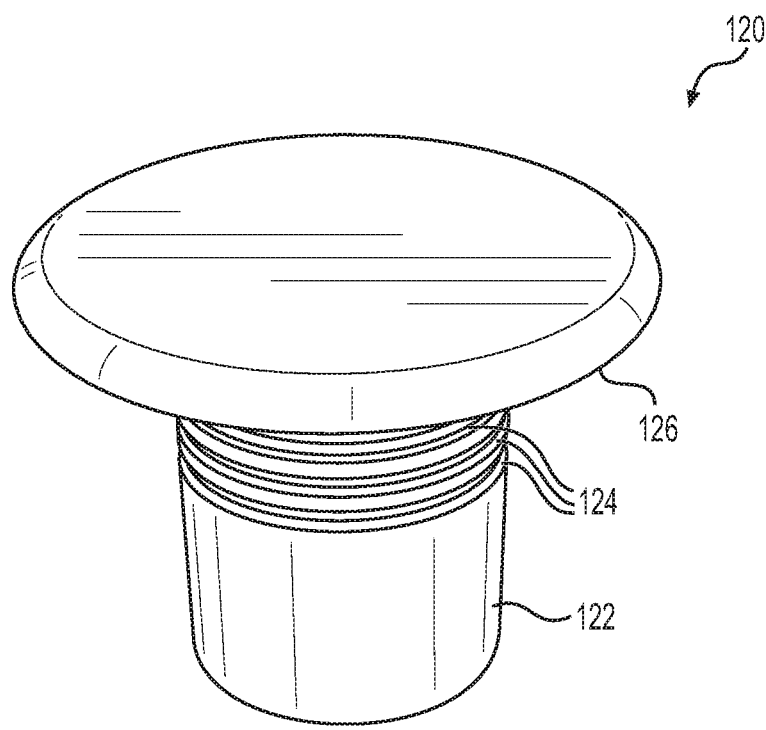
FIGS. 16-23 illustrate additional exemplary needle shield/guard grip device configurations, according to further aspects of the present disclosure.
Figure 17:
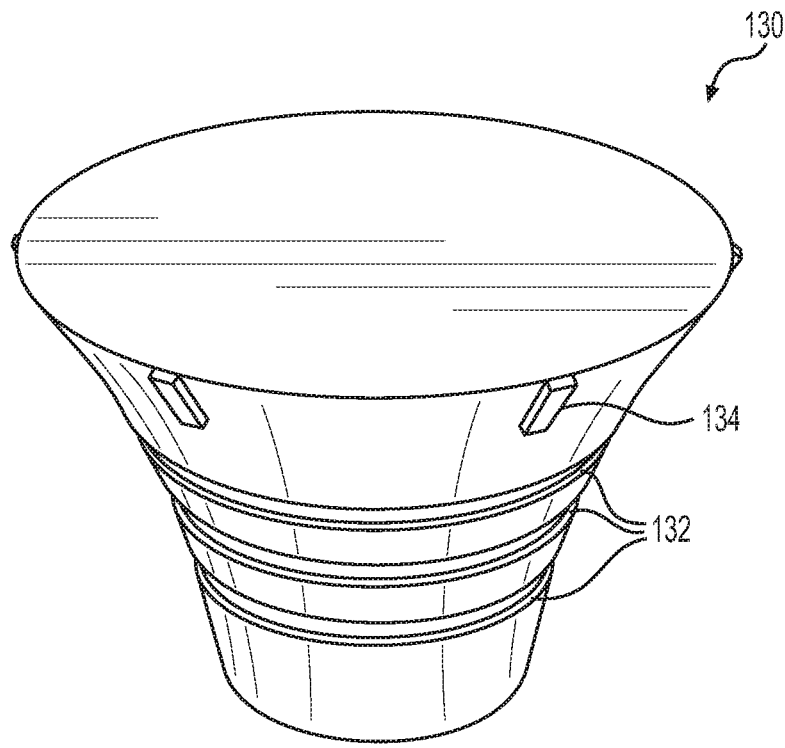
Figure 18:
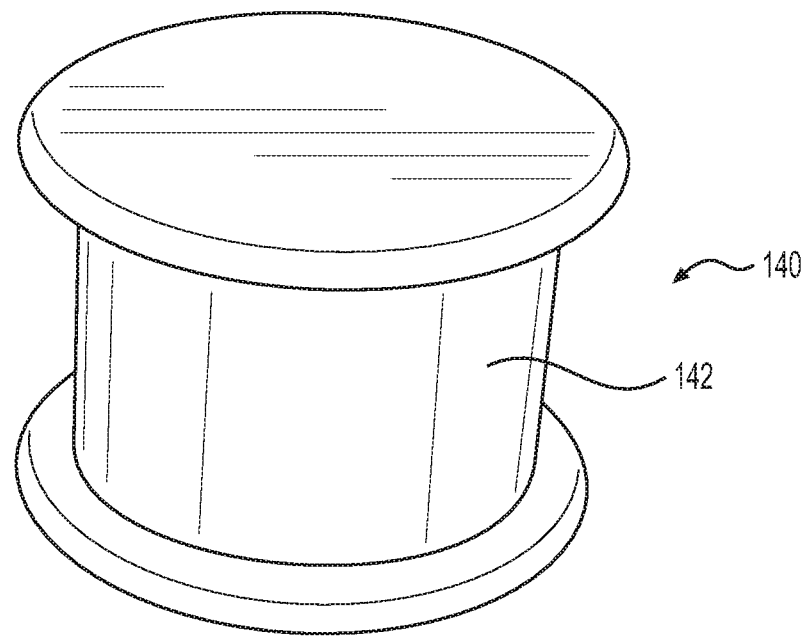
Figure 19:
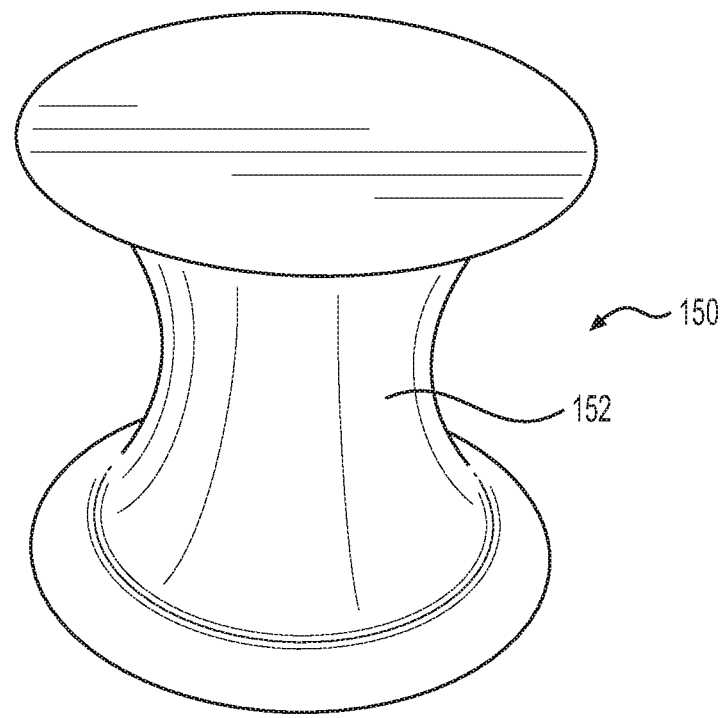
Figure 20:
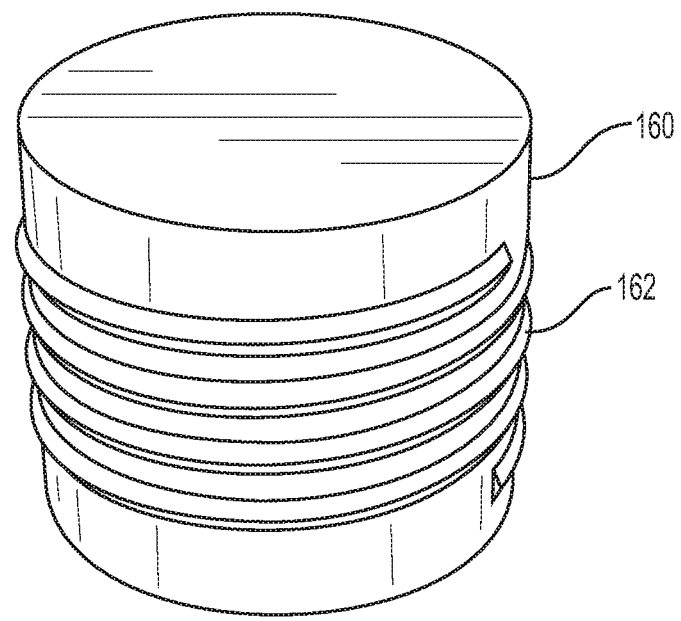
Figure 21:
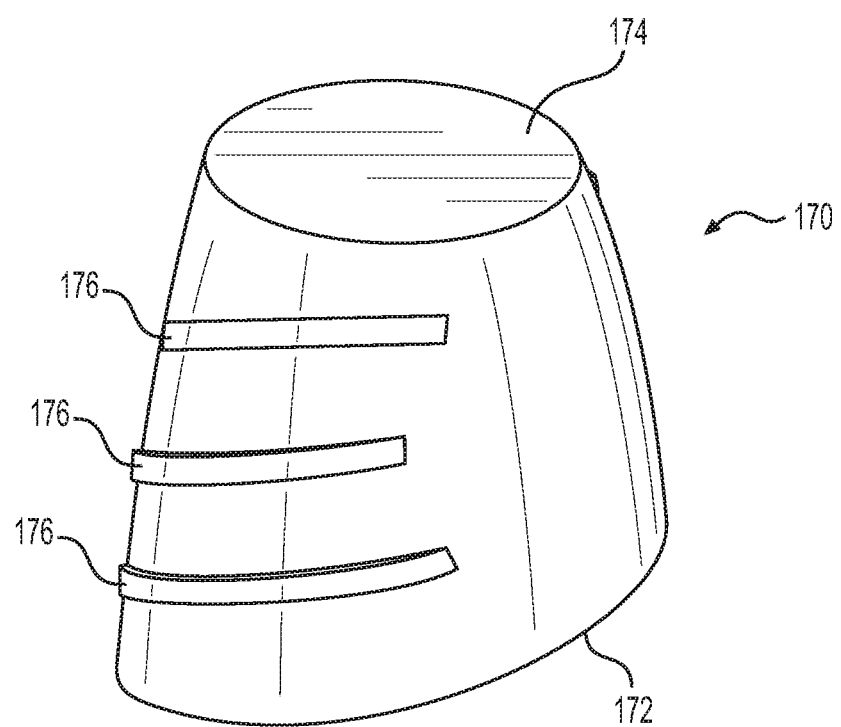
Figure 22:
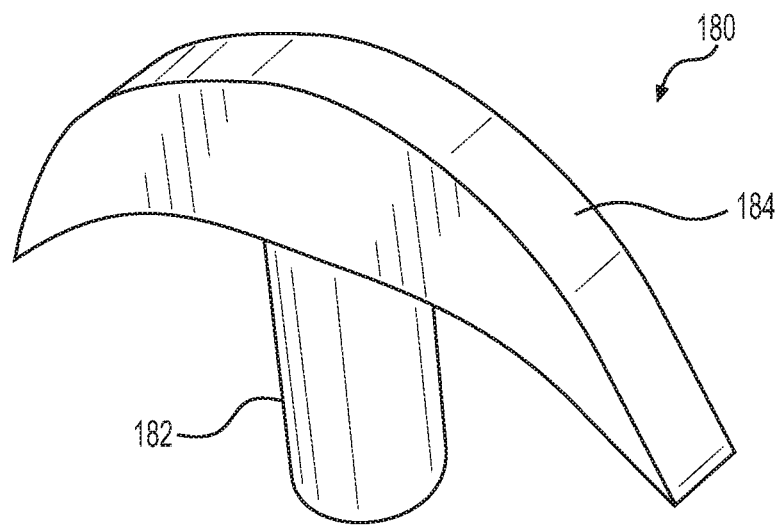
Figure 23:
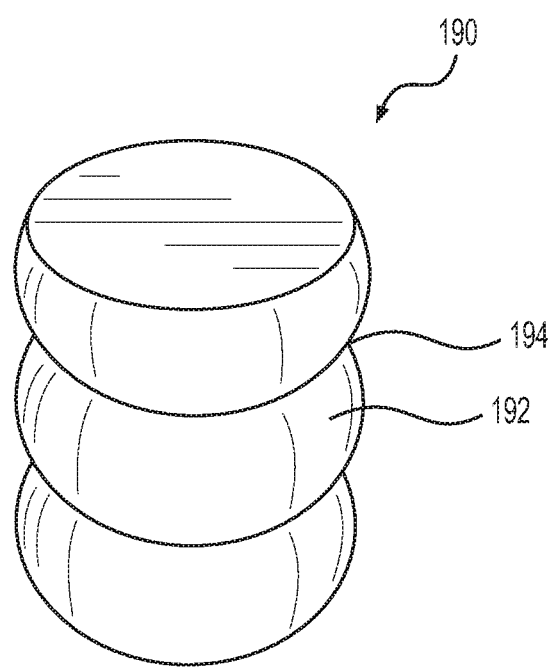

FIGS. 16-23 illustrate additional exemplary grip bodies, according to further aspects of the present disclosure and which may be used in conjunction with the principles described herein, including, e.g., retainer 80. That is, while exemplary grip bodies 50 and 100 are described above, it is understood that the disclosure is not so limited. Rather, the grip body may be shaped in any appropriate manner to facilitate grasping by an individual for removal thereof. For example, as shown in FIG. 16, a grip body 120 may include a mushroom shaped cap including a body 122 having a ribs 124 or the like positioned thereon. Additionally, grip body 120 may include a cap 126 under which a user may wrap his or her fingers for secure grasping. Grip body 130, as shown in FIG. 17, includes a flared cylinder shape, similar to that of FIGS. 15A and 15B above. In contrast to grip body 100, however, grip body 130 may include a plurality of ribs 132 extending about the perimeter of grip body 130 and general orthogonal to the longitudinal axis of grip body 130. Additionally, as shown in FIG. 17, grip body 130 may include a second plurality of ribs 134 or the like. As shown, ribs 132 and second ribs 134 may each have a varied shape so as to provide multiple forms of texture to grip body 130. FIGS. 18 and 19 illustrate a grip body 140 shaped as a standard spool (e.g., a spool of thread) and a curved spool 150, respectively. In use, a user may grasp a center 142 of spool grip body 140 or a center 152 of curved spool grip body 150 in order to remove grip body 140 or grip body 150 form syringe 12 so as to expose needle 14. FIG. 20 illustrates a generally cylindrical grip body 160 having a helical rib 162 extending about an exterior surface thereof. Additionally, FIG. 21 illustrates an irregularly shaped grip body 170, extending between a first end face along a plane angled with respect to a longitudinal axis of grip body 170 and a second end face along a plane orthogonal with respect to the longitudinal axis of grip body 170. A plurality of ribs 176 may be positioned about grip body 170 between first end face 172 and second end face 174. Optionally, as illustrated in FIG. 22, a grip body 180 may include a main body 182 and a hook-shaped pull 184 about which a user may wrap his or her finger about. In some arrangements, illustrated in FIG. 23, a grip body 190 may include a deformable surface 192. Deformable surface 192 may include one or more recesses 194 within which a user may wrap his or fingers.

Figure 26:
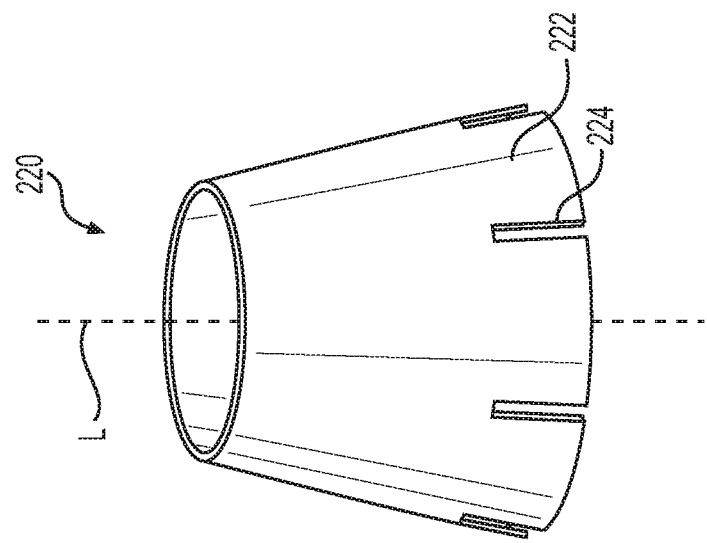
FIGS. 24-26 illustrate additional exemplary retainer devices, according to further aspects of the present disclosure.
Figure 25:
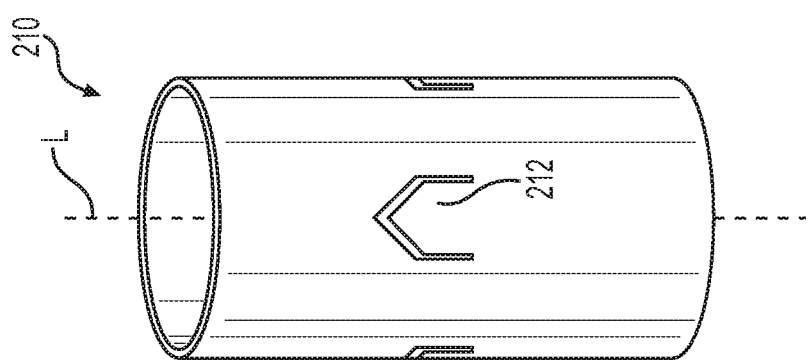
Figure 24:
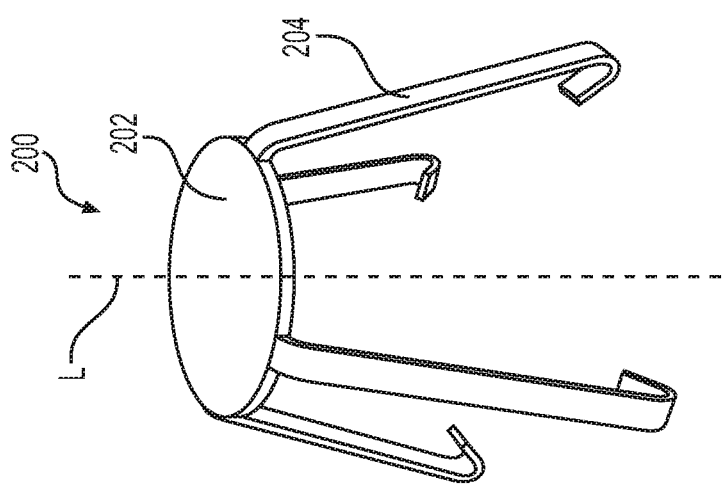

FIGS. 24-26 illustrate additional exemplary retainer devices, according to aspects of the present disclosure. For example, while retainer 80 is described as containing a generally rectangular base, in some arrangements, a retainer 200 may include a generally circular or disc shaped base 202 from which a plurality (e.g., four) arms 204 may depend. As shown, each arm 204 may be equidistantly spaced from one another about a longitudinal axis L of retainer 200. While four equidistant arms 204 are shown, it is understood that any number or spacing (e.g., equidistant or non-equidistant) of arms 204 may be used without departing from the scope of this disclosure. Alternatively, any one or more of the grip bodies described herein may be used in conjunction with retainer 210 or 220 (FIGS. 25 and 26, respectively). As shown in FIG. 25, retainer 210 may be cylindrical and include a plurality of cut outs or tabs 212 positioned thereon. Each tab 212 may be bent or otherwise deflected radially inwardly toward longitudinal axis L so as to grasp or otherwise interact with protrusions 36 of needle shield 30 and have any appropriate shape (e.g., polygonal, irregular, etc.). Alternatively, as shown in FIG. 26, retainer 220 may be a truncated cone and include a plurality of deflectable leaves 222 separated by slits 224. Leaves 222 may be inwardly compressed toward longitudinal axis L due to slits 224 for interaction with shield 30, and have any appropriate shape (e.g., polygonal, irregular, etc.).

Figure 27:
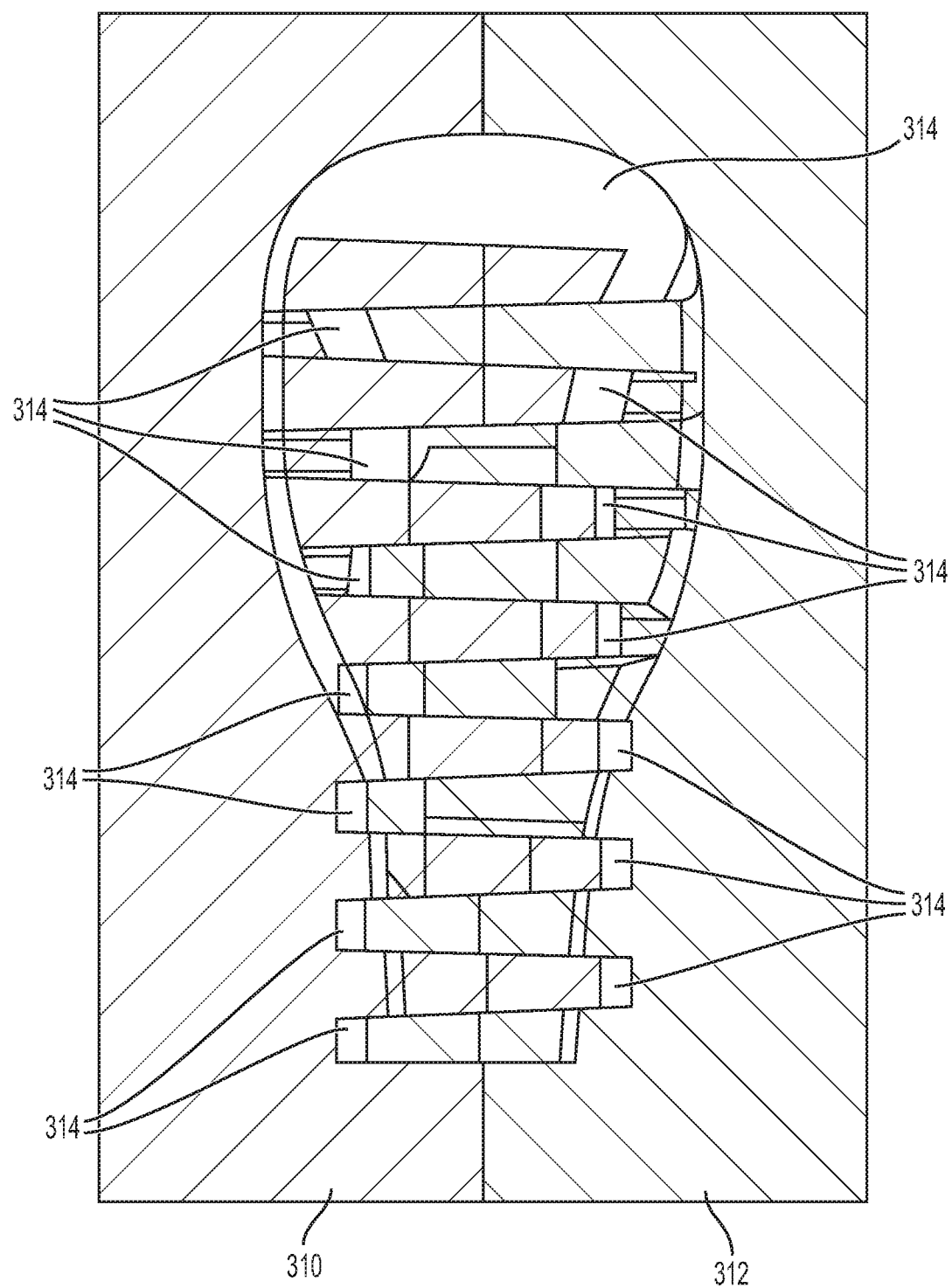
FIG. 27 illustrates a cross-sectional view of an exemplary mold for production of the needle shield/guard grip device of FIGS. 9-13.
Figure 28:
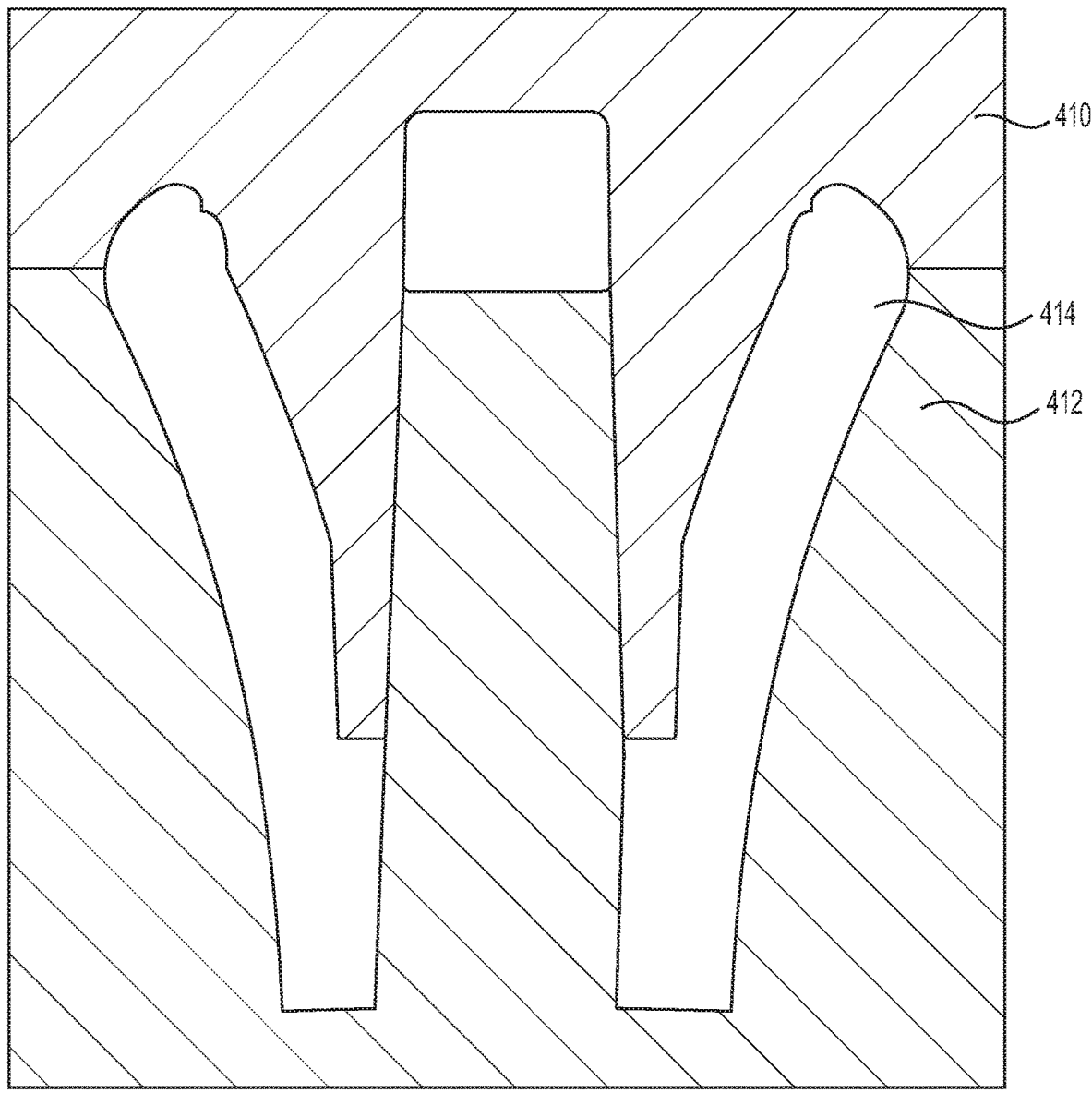
FIG. 28 illustrates a cross-sectional view of an exemplary mold for production of the needle shield/guard grip device of FIGS. 15A and 15B.

Any of grip bodies 50 and 100 may be formed entirely via a molding process, e.g., a single molding process, including, but not limited to, injection molding, die-casting, and/or compression molding. That is, body 50, including shoulder 77, may be formed without the need for supplemental cutting or carving of interior cavity 70, or spaces 62, thereby reducing manufacturing complexity, time, and/or expense. Particularly, grip body 50 and grip body 100 may be formed without the need for a side-action mold structure (e.g., a mold structure that acts from the outside of the part, generally moving in a direction perpendicular to a direction of a mold opening) so as to form inner cavity 70 (FIGS. 5-10 and 12) or inner cavity 110 (FIGS. 15A and 15B). For example, as shown in FIG. 27, molding of grip body 50 may include approximating mold portions 310 and 312 toward one another. In doing so, mold portions 310 and 312, shown in cross-section, may interdigitate (e.g., interlock) with one another so as to form a molding space 314 therebetween. Space 314 may be injected with thermoplastic material so as to form grip body 50, including shoulder 77, without the need for any additional side action molding portion, cutting, or other such further processing step. Similarly, as shown in FIG. 28, molding of grip body 100 may include approximating mold portions 410 and 412, shown in cross-section, toward one another so as to form a molding space 414 therebetween. Space 414 may be injected with thermoplastic material so as to form grip body 100, including shoulder 116, without the need for any additional side action molding portion, cutting, or other such further processing step. That is, manufacture of the mold bodies 50 and 100 is improved by reducing the complexity and cost required to produce mold bodies 50 and 100.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. For example, any of the described grip bodies disclosed herein may be used with any appropriate retainer described herein and vice versa. In addition, features described in connection with any grip body disclosed herein may be optionally used with or omitted from any other grip body disclosed herein. Accordingly, the present disclosure is not to be considered as limited by the foregoing description.

We claim:

1. A needle guard grip device, comprising:
   a body extending from a first end to a closed second end along a central longitudinal axis of the body, wherein the body further comprises:
   a plurality of ribs extending perpendicularly to the central longitudinal axis, wherein the plurality of ribs includes a first set of longitudinally spaced ribs disposed on a first side of the central longitudinal axis, and a second set of longitudinally spaced ribs disposed on a second side of the central longitudinal axis that is opposite of the first side, wherein, moving along the central longitudinal axis, ribs of the first set of longitudinally spaced ribs alternate with ribs of the second set of longitudinally spaced ribs; and
   an interior cavity extending from an opening in the first end of the body to a closed wall, wherein the closed wall extends perpendicularly to the central longitudinal axis and is longitudinally offset from the closed second end of the body;
   wherein one rib of the plurality of ribs is positioned closer to the closed second end of the body than the closed wall, and wherein a first rib of the first set of longitudinally spaced ribs includes a convex external surface, and wherein a second rib of the first set of longitudinally spaced ribs includes a concave external surface; and
   a retainer disposed within the interior cavity and having a tab extending from a portion of the retainer closest to the first end of the body, wherein the tab extends toward the central longitudinal axis and at an angle to the central longitudinal axis.

2. The needle guard grip device of claim 1, wherein adjacent ribs of the plurality of ribs are separated from one another by an opening into the body.

3. The needle guard grip device of claim 1, wherein the first rib is positioned closer to the first end of the body than the closed second end of the body.

4. The needle guard grip device of claim 3, wherein the second rib is positioned closer to the closed second end of the body than the first end of the body.

5. The needle guard grip device of claim 1, wherein the first rib is deflected radially outward away from the central longitudinal axis and is one rib of a first group of ribs that include convex external surfaces.

6. The needle guard grip device of claim 5, wherein the second rib is deflected radially inward toward the central longitudinal axis and is one rib of a second group of ribs that include concave external surfaces.

7. The needle guard grip device of claim 1, wherein each rib of the plurality of ribs extends from a first side wall of the body to a second side wall of the body.

8. The needle guard grip device of claim 1, wherein the retainer is a clip having an opposing pair of arms, wherein each arm of the opposing pair of arms extends at an angle relative to the central longitudinal axis of the body.

9. The needle guard grip device of claim 1, wherein the closed second end of the body has a bulbous shape and the closed wall has a planar shape, the bulbous shape has a cross-sectional dimension that is greater than a cross-sectional dimension of the closed wall, and the retainer is positioned entirely within the interior cavity of the body and flush against the closed wall.

10. The needle guard grip device of claim 1, wherein the retainer is a clip having an opposing pair of arms connected together by a planar surface extending perpendicularly to the central longitudinal axis.

11. A needle guard grip device, comprising:
a body extending from a first end to a closed second closed end along a central longitudinal axis of the body, the body comprising:
   a plurality of ribs, wherein (i) a first group of ribs of the plurality of ribs have convex external surfaces and (ii) a second group of ribs of the plurality of ribs have concave external surfaces; and
   an interior cavity extending from an opening in the first end of the body to a closed wall, wherein the closed wall extends perpendicularly to the central longitudinal axis and is longitudinally offset from the closed second end of the body; and
a clip disposed within the interior cavity, wherein the clip includes a planar surface extending perpendicularly to the central longitudinal axis, a pair of arms depending from the planar surface and extending towards the first end of the body, wherein a first arm of the pair of arms includes a tab extending away from the first arm and toward the central longitudinal axis;
wherein the closed second end of the body has a bulbous shape and the closed wall of the interior cavity has a planar shape, the bulbous shape of the closed second end has a cross-sectional dimension that is greater than a respective cross-sectional dimension of each of the first end and the closed wall, and the wall is configured to engage the planar surface of the clip.

12. The needle guard grip device of claim 11, wherein each arm of the pair of arms extends towards the first end of the body at an angle to the central longitudinal axis.

13. The needle guard grip device of claim 11, wherein a rib of the plurality of ribs lies in a plane perpendicular to the central longitudinal axis.

14. The needle guard grip device of claim 11, wherein the tab extends towards the closed second end of the body at an angle to the central longitudinal axis.

15. The needle guard grip device of claim 11, wherein the first end of the body has a first cross-sectional dimension and the closed second end of the body has a second cross-sectional dimension larger than the first cross-sectional dimension, and the closed second end of the body is closed and longitudinally offset from the closed wall.

16. A needle guard grip device, comprising:
a body extending from a first end to a closed second closed end along a central longitudinal axis of the body, wherein the body further comprises:
   a plurality of ribs extending perpendicularly to the central longitudinal axis, wherein the plurality of ribs includes a first set of longitudinally spaced ribs disposed on a first side of the central longitudinal axis, and a second set of longitudinally spaced ribs disposed on a second side of the central longitudinal axis that is opposite of the first side, wherein, moving along the central longitudinal axis, ribs of the first set of longitudinally spaced ribs alternate with ribs of the second set of longitudinally spaced ribs; and
   an interior cavity extending from an opening in the first end of the body to a closed wall, wherein the closed wall extends perpendicularly to the central longitudinal axis and is longitudinally offset from the closed second end of the body;
wherein one rib of the plurality of ribs is positioned closer to the second end of the body than the closed wall, and wherein a first rib of the first set of ribs is deflected radially outward away from the central longitudinal axis, and wherein a second rib of the first set of ribs is deflected radially inward toward the central longitudinal axis; and
a retainer disposed within the interior cavity and having a tab extending from a portion of the retainer closest to the first end of the body, wherein the tab extends toward the central longitudinal axis and at an angle to the central longitudinal axis.

17. The needle guard grip device of claim 16, wherein the first rib of the first set of ribs has a first lateral length, and the first rib is deflected radially outward away from the central longitudinal axis along an entirety of the first lateral length; and
wherein the second rib of the first set of ribs has a second lateral length, and the second rib is deflected radially inward toward the central longitudinal axis along an entirety of the second lateral length.

18. The needle guard grip device of claim 16, wherein the closed second end of the body is closed and longitudinally offset from the closed wall, wherein the closed wall closes the internal cavity opposite of the opening at the first end.

19. The needle guard grip device of claim 16, wherein the closed second end of the body has a bulbous shape, and the closed wall has a planar shape that is configured to engage the retainer, the planar shape of the closed wall has a cross-sectional dimension that is smaller than a cross-sectional dimension of the bulbous shape of the closed second end.

20. The needle guard grip device of claim 16, wherein the first rib of the first set of ribs has a convex external surface, and the second rib of the first set of ribs has a concave external surface.

* * * * *

UNITED STATES PATENT AND TRADEMARK OFFICE
CERTIFICATE OF CORRECTION

| | | |
|---|---|---|
| PATENT NO. | : 11,478,588 B2 | Page 1 of 1 |
| APPLICATION NO. | : 16/574327 | |
| DATED | : October 25, 2022 | |
| INVENTOR(S) | : Bryan C. Grygus, Richard Jeff Gildersleeve, Jr. and Shaina Varghese | |

It is certified that error appears in the above-identified patent and that said Letters Patent is hereby corrected as shown below:

In the Claims

In Column 15, Lines 2-3 of Claim 11, delete "closed second closed" and insert --closed second--.

In Column 15, Line 26 of Claim 11, delete "the wall" and insert --the closed wall--.

In Column 15, Lines 44-45 of Claim 16, delete "closed second closed" and insert --closed second--.

In Column 16, Line 14 of Claim 16, delete "second end" and insert --closed second end--.

Signed and Sealed this
Sixth Day of December, 2022

*Katherine Kelly Vidal*

Katherine Kelly Vidal
*Director of the United States Patent and Trademark Office*